(12) United States Patent  (10) Patent No.: US 9,241,710 B2
Paz et al.  (45) Date of Patent: Jan. 26, 2016

(54) SURGICAL FASTENERS AND FASTENING DEVICES

(75) Inventors: Adrian Paz, Petach Tikva (IL); Gilad Heftman, Kibbutz Ein Gev (IL)

(73) Assignee: I.B.I ISRAEL BIOMEDICAL INNOVATIONS LTD., Caesarea Industrial Park (IL)

( * ) Notice: Subject to any disclaimer, the term of this patent is extended or adjusted under 35 U.S.C. 154(b) by 1596 days.

(21) Appl. No.: 11/988,293

(22) PCT Filed: Jul. 6, 2006

(86) PCT No.: PCT/IL2006/000783
§ 371 (c)(1),
(2), (4) Date: Feb. 13, 2009

(87) PCT Pub. No.: WO2007/004228
PCT Pub. Date: Jan. 11, 2007

(65) Prior Publication Data
US 2009/0182352 A1  Jul. 16, 2009

Related U.S. Application Data

(60) Provisional application No. 60/696,516, filed on Jul. 6, 2005.

(51) Int. Cl.
*A61B 17/064* (2006.01)
*A61B 17/068* (2006.01)
(Continued)

(52) U.S. Cl.
CPC ......... *A61B 17/0643* (2013.01); *A61B 17/0644* (2013.01); *A61B 17/0682* (2013.01);
(Continued)

(58) Field of Classification Search
CPC .. A61B 17/122; A61B 17/128; A61B 17/064; A61B 17/0644; A61B 17/0643; A61B 17/08; A61B 17/0642; A61B 17/068; A61B 2017/0641; A61B 2017/0645; F16B 15/00; F16B 15/0015; F16B 15/08; F16B 15/04; F16B 15/02
USPC ........... 606/151, 153–155, 219, 220, 213, 75, 606/142, 143, 157; 411/457–476
See application file for complete search history.

(56) References Cited

U.S. PATENT DOCUMENTS 919,631 A * 4/1909 Page ............................ 411/471
3,908,662 A * 9/1975 Razgulov et al. ............. 606/149
(Continued)

FOREIGN PATENT DOCUMENTS

JP  5-317325 A  12/1993
JP  11-56859 A  3/1999
(Continued)

OTHER PUBLICATIONS

International Search Report; dated Oct. 26, 2006.
(Continued)

*Primary Examiner* — Christopher L Templeton
(74) *Attorney, Agent, or Firm* — Dorsey & Whitney LLP

(57) ABSTRACT

The invention provides a surgical fastener. The fastener has a first element defining an axis of the fastener, and one or more prongs attached to the first element at hinge regions. Deploying the fastener involves bending the prongs at the hinges so as to increase the distance of the prong tips from the axis and locking the fastener in this deployed configuration. The invention also provides a surgical fastening device and a method for attaching a surgical fastener to a site of a body tissue.

21 Claims, 44 Drawing Sheets

(51) Int. Cl.
*A61B 17/122* (2006.01)
*A61B 17/128* (2006.01)
*A61B 17/04* (2006.01)

(52) U.S. Cl.
CPC ............. *A61B17/064* (2013.01); *A61B 17/122* (2013.01); *A61B 17/128* (2013.01); *A61B 2017/0409* (2013.01); *A61B 2017/0412* (2013.01); *A61B 2017/0422* (2013.01); *A61B 2017/0427* (2013.01); *A61B 2017/0641* (2013.01)

(56) References Cited

U.S. PATENT DOCUMENTS

| | | | | |
|---|---|---|---|---|
| 3,925,955 | A * | 12/1975 | Becht | 411/472 |
| 4,741,336 | A * | 5/1988 | Failla et al. | 227/181.1 |
| 5,189,766 | A * | 3/1993 | Weber | 24/459 |
| 5,234,447 | A * | 8/1993 | Kaster et al. | 606/153 |
| 5,470,010 | A | 11/1995 | Rothfuss et al. | |
| 5,478,353 | A * | 12/1995 | Yoon | 606/213 |
| 5,582,616 | A | 12/1996 | Bolduc et al. | |
| 5,667,527 | A * | 9/1997 | Cook | 606/219 |
| 5,810,882 | A | 9/1998 | Bolduc et al. | |
| 5,830,221 | A | 11/1998 | Stein et al. | |
| 5,964,782 | A * | 10/1999 | Lafontaine et al. | 606/213 |
| 6,126,372 | A * | 10/2000 | Takata | 411/513 |
| 6,193,734 | B1 * | 2/2001 | Bolduc et al. | 606/153 |
| 6,200,330 | B1 * | 3/2001 | Benderev et al. | 606/232 |
| 6,206,913 | B1 * | 3/2001 | Yencho et al. | 623/1.3 |
| 6,371,964 | B1 * | 4/2002 | Vargas et al. | 606/153 |
| 6,666,873 | B1 | 12/2003 | Cassell | |
| 6,682,540 | B1 | 1/2004 | Sancoff et al. | |
| 6,776,784 | B2 * | 8/2004 | Ginn | 606/151 |
| 7,118,318 | B2 * | 10/2006 | Ryals et al. | 411/475 |
| 7,316,706 | B2 * | 1/2008 | Bloom et al. | 606/232 |
| 7,833,238 | B2 * | 11/2010 | Nakao | 606/151 |
| 2004/0034357 | A1 * | 2/2004 | Beane et al. | 606/73 |
| 2004/0044364 | A1 | 3/2004 | DeVries et al. | |
| 2004/0078054 | A1 | 4/2004 | Biggs et al. | |
| 2005/0109888 | A1 * | 5/2005 | Ryals et al. | 248/71 |
| 2005/0158360 | A1 * | 7/2005 | Falotico et al. | 424/424 |
| 2006/0030881 | A1 * | 2/2006 | Sharkey et al. | 606/213 |

FOREIGN PATENT DOCUMENTS

| | | |
|---|---|---|
| JP | 2004-160177 A | 6/2004 |
| JP | 2004-329964 A | 11/2004 |
| WO | 2005/004727 A1 | 1/2005 |

OTHER PUBLICATIONS

European Search Report; dated Nov. 20, 2009.

* cited by examiner

SURGICAL FASTENERS AND FASTENING DEVICES

CROSS-REFERENCE

This is a National Phase Application filed under 35 U.S.C. 371 of International Application No. PCT/IL2006/000783, filed Jul. 6, 2006, claiming the benefit under 35 USC 119(e) of U.S. Provisional Application No. 60/696,516, filed Jul. 6, 2005, the entire content of each of which is hereby incorporated herein by reference in its entirety.

FIELD OF THE INVENTION

This invention relates to surgical fasteners and to surgical fastening devices.

BACKGROUND OF THE INVENTION

Surgical anchors are used instead of surgical suturing, which is often both time consuming and inconvenient, in order to join two tissue locations. A surgeon can often use a stapling apparatus to implant an anchor into a body tissue and thus accomplish in a few seconds, what would take a much longer time to suture. A surgical anchor is used, for example in inguinal hernia surgery to fasten polypropylene mesh to the abdominal wall in order to reinforce the abdominal wall.

Conventional surgical fasteners have been in the form of ordinary metal staples, which are bent by the delivery apparatus to join together body tissues. These staples comprise a pair of legs or prongs joined together at one end by a crown that may be straight or arcuate. During deployment of the staple, the prongs are inserted into a tissue and are then made to bend inwards towards.

At present, there are a variety of surgical fasteners and fastening devices available for endoscopic or open procedures, to attach tissues together, or to attach a mesh patch to a tissue. One such surgical fastener is a surgical stapler, or clip applicator. In this stapler, a plurality or stack of unformed staples are contained within a cartridge and are sequentially advanced or fed within the instrument by a spring mechanism. A secondary feeding mechanism is employed to separate the distal most staple from the stack, and to feed the distal most stapler into the staple closing mechanism. Such mechanisms are found in U.S. Pat. Nos. 5,470,010, and 5,582,616.

In some applications, the body tissue is accessible from two opposite direction so that an anvil may be used to deform the legs of a staple after having passed through the body tissue. In applications where access to the tissue is from only one direction, an anvil may be used to deform the crown of a conventional staple so that the legs project towards each other in the body tissue so as to hold the staple in the tissue.

Another stapler mechanism, used mostly for mesh attachment to tissue does not use an anvil. Instead, a fastener comprising a helical wire is screwed or rotated into a tissue, in order to join tissues to affix a polypropylene or similar material mesh or other patch to the tissue together. Instruments and fasteners of this type are found in U.S. Pat. No. 5,582,616, U.S. Pat. No. 5,810,882, and U.S. Pat. No. 5,830,221. Another type of fastener that does not need an anvil applies fasteners made from a shape memory alloy such as Nitinol™. These fasteners are mainly used to fasten prosthetic material or artificial mesh to tissue.

These fasteners and fastening devices suffer from significant drawbacks especially when attaching fasteners to soft tissue. The strength of attachment of these devices depends mainly on the content and size of collagen fibers. Most soft tissue, such as subcutaneous tissue and fatty tissue surrounding internal organs, has few and slender collagen fibers and hence the attachment of the common art fasteners to such tissue is weaker than attachment to stronger tissues such as fascia or ligaments, which have more and larger collagen fibers.

There is a need for a fastener that permits a stronger attachment to such soft tissue by attaching to a large surface.

There is a need for a fastener that has a narrow profile before deployment and increases to a large radius in the deployed state by extension of radial prongs for grasping the soft tissue.

There is a need for a fastener in which the extension of the prongs is performed by applying forces within the fastening instrument only and not by forcing the device against the tissue, by penetrating the tissue, or by pulling the device through tissue, actions which may cause inadvertent injury to tissue and improper attachment.

There is a need for a fastener that can attach a graft or mesh to such soft tissues.

There is a need for a fastener that can retain its deployed configuration despite forces that tend to detach it, preferably by providing locking means within the fastener.

There is a need for a fastening device that can deploy one or a stack of such fasteners.

There is a need for a fastening device, which can deploy a fastener by applying forces only within the fastening device without the need to apply forces on the tissue.

There is a need for a fastening device, in which the deployment and release of the fastener are performed by separate means.

There is a need for a fastening device that can grasp a mesh or a graft, bring it to the desired location and attach it to soft tissue by deploying a fastener.

SUMMARY OF THE INVENTION

In its first aspect the invention provides a surgical fastener. The surgical fastener of the invention comprises two or more prongs each of which is connected to a first element by a hinge. The fastener is positioned at the site of a tissue surface where it is to be deployed. The fastener is then deployed by applying an extending force to the prongs so that the prongs splay radially outward from the first element by rotating at the hinges as they enter the body tissue so as to become embedded in the tissue. The fastener may be used to attach a graft or a mesh to a body tissue. In contrast to the prior art surgical anchors which penetrate the tissue entirely, in the case of the surgical fastener of the present invention, only the prongs of the fastener penetrate through the graft or mesh into the tissue, while the first element to which the prongs are connected attach the graft or mesh to the tissue surface without penetrating into it.

The first element or crown, may have any shape, as required in any application. For example, the first element may have a shape such as a flat disk, a rectangular or polygonal shaped flat surface, an irregularly shaped flat surface, an annular ring, a cylindrical ring, or a cylinder.

The fastener may contain any number of prongs that is at least two. The prongs may have any profile as required in any application, such as a rectangular profile, a round profile, an oval profile, a triangular profile, or an elliptical profile. The prongs may be straight or curved with constant or variable curvature. The prongs may be manufactured integrally with the first element. In this case an integral hinge is formed at the attachment site of each prong to the first element. The integral hinge may be formed, for example, as a region of decreased thickness or width of the prong, or by a perforation in the prong. The prongs may be manufactured separately from the first element and then attached to the first element, for example, using an adhesive. Alternatively, the prongs may be attached to the first element by a two-part hinge, for example, a two-part hinge formed by hooking the prongs onto the first element. The prongs may have blunt tips, pointed tips or barbed tips, as required in any application.

In some embodiments, the fastener includes a second element or baseplate. In these embodiments, the prong tips are inserted into slots in the second element. In an undeployed configuration the prongs tips are engaged within the slots in the second element or protrude minimally beyond the second element plane and the prongs are held in this position due to an engagement between the prongs and the second element, for example, by friction between the prongs and slot edges or by adhesive, glue or by a plug of softer material such as a biodegradable material. A fastening device is deployed by urging the first element towards the base. As the prongs pass through the slots, the force applied to the prongs by the slot edges causes them to rotate at the hinge and splay radially outward from the crown. The second element may have any shape, as required in any application. For example, the second element may be a baseplate having a shape such as a flat disk, a rectangular or polygonal shaped flat surface, an irregularly shaped flat surface, an annular ring, a cylindrical ring, or a cylinder.

The fastener of the invention may be manufactured from stainless steel, Nitinol, titanium or other biocompatible metallic alloys. It may be manufactured from biocompatible, and possibly biodegradable, plastic or metallic materials or a combination of such materials.

The fastener of the invention is locked in the deployed configuration in order to prevent unintended release of the fastener from the body tissue. As used herein, the term "locking" of the fastener refers to an engagement between components of the fastener that increases the force necessary to bend the extended prongs of the deployed fastener closer to the longitudinal axis of the fastener compared to situation in which such means are not provided. The result is that the fastener retains its deployed configuration despite the forces that act on it within the tissue and is better attached to the delicate soft tissue.

The locking may be due to an engagement between the prongs and the first element. If a second element is present in the fastener, the locking may be due to an engagement between the second element and the prongs or the second element and the first element. For example, the locking may result from increased friction between the prongs and slots due to a region along the length of the prongs of increased width or thickness that enters the slot during deployment, so that the prong becomes jammed in the slot. The prongs may be locked in the deployed configuration by engagement of a tongue extending from each slot of the second element into an opening in the prong. Alternatively, a tongue in the prong may engage an opening in the second element.

In its second aspect the invention provides a surgical fastening device for deploying a surgical fastener. The fastening device of the invention is configured to receive one or more fasteners to be deployed in a body tissue. The device is configured to apply an extending force to the prongs of the fastener to cause the prongs to splay radially outward from the first element by rotating at the hinges. The fastening device may have, for example, a slender hollow shaft containing a stack of one or more fasteners. In this case, the tip of the shaft is delivered to the body site where the fastener is to be deployed. As the fastener is brought to its deployed configuration by the fastening device, the prongs splay out from the first element into the body tissue at that site. Once the fastener has attained its deployed configuration, the fastener is released from the fastening device. The fastening device of the invention is preferably manufactured from biocompatible materials, such as biocompatible metallic or plastic materials, or a combination of them.

The surgical fastening device of the invention may have a slender shaft configured to receive a stack of surgical fasteners of the invention. A plunger inside the shaft is activated to deliver a force to the stack of fasteners that is transmitted to the fastener at the shaft tip. The shaft tip is configured to apply a counter force to this fastener so that the prongs of the fastener experience an extending moment to the prongs that brings the fastener into its deployed configuration. After deployment of the fastener, a releasing mechanism releases the deployed fastener from the fastening device. The shaft may be rigid, semi-rigid or flexible. It may be flexible along its entire length or only at specific locations thus permitting manipulation of the shaft in narrow body spaces.

In some embodiments, a surgical filament may pass through the fasteners or around the fasteners and may be grasped by the fastener when the fastener is deployed in a tissue. This filament may be used to bridge two or more fasteners attached to different tissues sites, for example, in order to approximate the different tissue sites. The filament may be a thread with any profile, a sheet of plastic material, or a net or mesh of plastic or metallic material. A sheet, net, or mesh may be used by enveloping it as a sleeve around the shaft of a fastening device. In this case, when a fastener is deployed at the shaft tip, the prongs pierce the sleeve from inside through the filament and then penetrate the tissue, thus fixing the sleeve to the tissue.

The term "deploying the fastener" means extending the prongs to their full extent in relation to the first element or the crown.

The term "releasing the fastener" means disengaging the fastening device from the deployed fastener.

Thus, in its first aspect, the present invention provides a surgical fastener having an undeployed configuration and a deployed configuration, comprising:
(a) a first element defining an axis of the fastener; and
(b) two or more prongs, each prong being attached to the first element at a hinge and each prong having a tip;
wherein, in the undeployed configuration, the tip of each prong is at a first distance from the axis that is greater than a distance of the prong's hinge from the axis; and
wherein, in the deployed configuration, the tip of each prong is at a second distance from the axis that is greater than the first distance and wherein the fastener is locked in the deployed configuration.

In its second aspect, the invention provides a surgical fastening device for deploying one or more surgical fasteners, each surgical fastener having an undeployed configuration and a deployed configuration, and comprising:
(a) a first element defining an axis of the fastener; and
(b) two or more prongs, each prong being attached to the first element at a hinge and each prong having a tip;
wherein, in the undeployed configuration, the tip of each prong is at a first distance from the axis that is greater than a distance of the prong's hinge from the axis; and
wherein, in the deployed configuration, the tip of each prong is at a second distance from the axis that is greater than the first distance;
the surgical fastening device comprising:
a. a receptacle adapted to receive one or more surgical fasteners in the undeployed configuration, and b. a deployment mechanism configured to bring a fastener in the receptacle to its deployed configuration by applying a first force to first element and a second force to the prongs wherein the second force is directed in a direction essentially opposite to the direction of the first force.

In its third aspect, the invention provides a surgical fastening system comprising:
(a) a surgical fastening device for deploying one or more surgical fasteners, each surgical fastener having an undeployed configuration and a deployed configuration, and comprising:
  (i) a first element defining an axis of the fastener; and
  (ii) two or more prongs, each prong being attached to the first element at a hinge and each prong having a tip;
  wherein, in the undeployed configuration, the tip of each prong is at a first distance from the axis that is greater than a distance of the prong's hinge from the axis; and wherein, in the deployed configuration, the tip of each prong is at a second distance from the axis that is greater than the first distance;
  the surgical fastening device comprising:
  a receptacle adapted to receive one or more surgical fasteners in the undeployed configuration,
  a deployment mechanism configured to bring a fastener in the receptacle to its deployed configuration by applying a first force to first element and a second force to the prongs wherein the second force is directed in a direction essentially opposite to the direction of the first force; and
  a releasing mechanism for disengaging the fastening device from the fully deployed fastener; and
(b) one or more surgical fasteners, each of the one or more surgical fasteners comprising:
  (iii) a first element defining an axis of the fastener; and
  (iv) two or more prongs, each prong being attached to the first element at a hinge and each prong having a tip;
  wherein, in the undeployed configuration, the tip of each prong is at a first distance from the axis that is greater than a distance of the prong's hinge from the axis; and wherein, in the deployed configuration, the tip of each prong is at a second distance from the axis that is greater than the first distance.

In its fourth aspect, the invention provides a method for attaching a surgical fastener to a site of a body tissue, the surgical fastener comprising
(a) a first element defining an axis of the fastener; and
(b) two or more prongs, each prong being attached to the first element at a hinge and each prong having a tip;
wherein, in the undeployed configuration, the tip of each prong is at a first distance from the axis that is greater than a distance of the prong's hinge from the axis; and wherein, in the deployed configuration, the tip of each prong is at a second distance from the axis that is greater than the first distance;
the method comprising applying an extending force to the prongs to fully deploy the fastener by forces exercised within the fastening instrument, wherein the extending prongs pierce a mesh or a graft and the adjacent tissue and the first element of the fastener attach said mesh or graft to the tissue.

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF PREFERRED EMBODIMENTS

Figure 1:
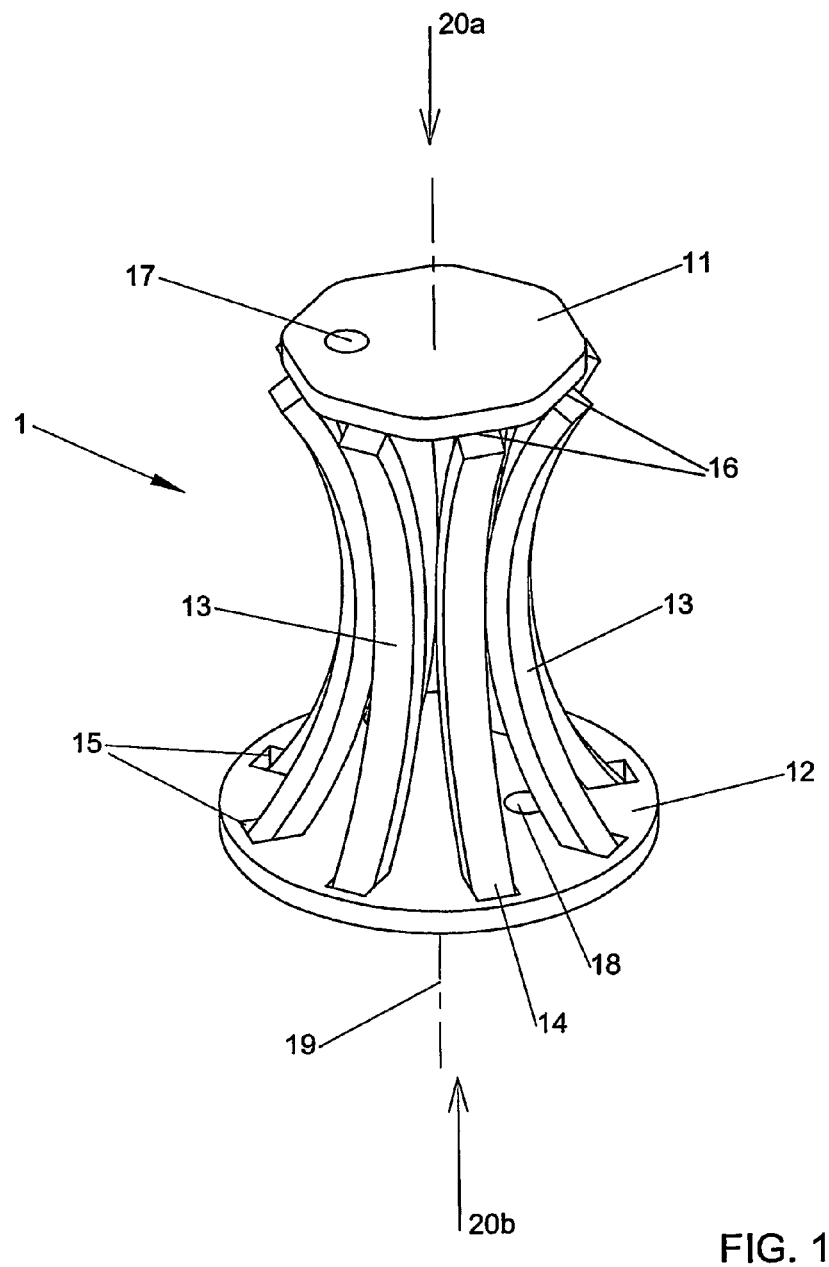
FIG. 1 shows a surgical fastener in an undeployed configuration according to one embodiment of the invention.
Figure 2:
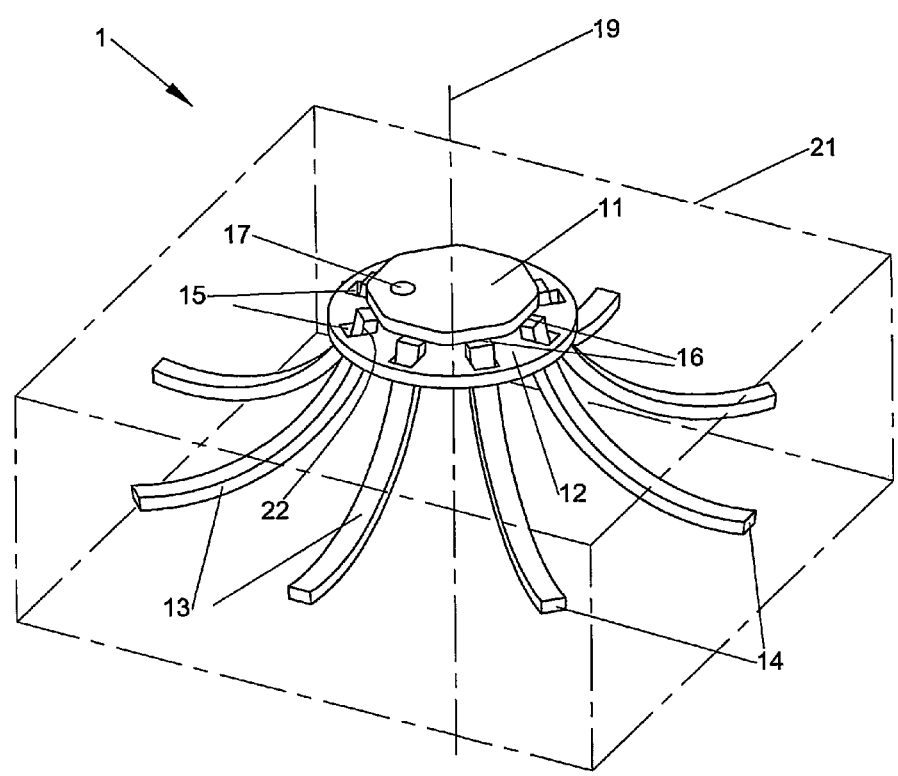
FIG. 2 shows the surgical fastener of FIG. 1 deployed in a tissue.

FIGS. 1 and 2 show a fastener 1 in accordance with one embodiment of the fastener of the invention. The fastener 1 is shown in FIG. 1 in its undeployed configuration from a side perspective view. The fastener 1 is shown in FIG. 2 in its deployed configuration in a tissue 21 from a side perspective view. The tissue 21 is indicated by broken lines in FIG. 2. The fastener 1 has a first element in the form of a flat crown 11. The fastener 1 also has a second element in the form of a flat baseplate 12. Two or more prongs 13 extend from the crown 11 at hinge regions 16. Each hinge region 16 is a weakened region at the attachment site of each prong 13 to the crown 11. The integral hinge 16 between the crown 11 and prongs 13 may be formed by attachment of the prongs to the crown with biocompatible glue or adhesive that is weaker than the material of the crown and prongs. In this embodiment, the crown 11 is integrally formed with the prongs 13. Eight prongs 13 are shown in FIG. 1, but this is by way of example only and the fastener 1 may have any number of prongs 13 that is greater than or equal to 2. Each prong 13 terminates in a tip 14. The baseplate 12 has a number of slots 15 through which the tips 14 of the prongs 13 pass in the assembled fastener 1 in the undeployed conformation (FIG. 1).

In order to mount the crown 11 on the base 12, the prongs 13 are bent at the hinge regions 16 in order to bring the prongs close to an axis 19 of the fastener 1. In this configuration, the tips 14 are inserted into slots 15 in the baseplate 12, as shown in FIG. 1.

The fastener 1 is applied to the surface of a body tissue and deployed. Deploying the fastener 1 involves moving the crown 11 relative to the baseplate 12 along the axis 19 so as to decrease the separation of the crown 11 and the baseplate 12. This is accomplished by applying a normal force on the crown 11 directed towards the baseplate 12 as indicated by the arrow 20a and a counterforce on the baseplate 12 in the opposite direction indicated by the arrow 20b. These forces urge the crown 11 toward the baseplate 12. As the crown 11 approaches the baseplate 12, the prongs 13 experience an extending movement by the edges of the slots 15 that causes the prongs 13 to rotate at the hinge region 16 and move in a radially outward direction from the crown 11 penetrating the body tissue 21, while the crown 11 and baseplate 12 remain at the surface. This extending of the prongs at the hinge region is due to the fact that the hinge regions 16 are weaker than the rest of the prongs 13 and that the moment acting in the prong during deployment is maximal at the hinge. A a weaker hinge region lowers the force required within a fastening device to extend the prongs during deployment. This force depends on the resistance of the hinges to the extending moment. Weak hinge means low resistance. As the crown 11 moves toward the base 12, the prongs 13 advance through the slots 15. The hinge regions 16 are located at a distance from the center of the crown 11 that is less than the distance between the slots 15 and the center of the baseplate 12. Thus, as the prongs 13 pass through the slots 15, the prongs tips move through a curved trajectory and the prongs 13 splay outward from the baseplate 12 in the deployed configuration shown in FIG. 2. During deployment of this embodiment there is no deformation of the crown 11, the prongs 13 or the baseplate 12.

A hole 17 in the crown 11 and a hole 18 in the baseplate may be provided for permitting the passage of a filament through the fastener 1. The holes 17 and 18 may be coaxial, or may not be coaxial, as shown in FIG. 1. The filament may be grasped between the baseplate of the deployed fastener and the tissue surface. When the holes 17 and 18 are not coaxial the filament may also be grasped between the crown 11 and the baseplate 12.

Only the integral hinge 16 undergoes plastic deformation. This plastic deformation of the hinge 16 maintains the fastener 1 in its deployed configuration. When a pulling force is applied to the baseplate 12 of the fastener 1 attached to a body tissue 21, for example, by puling on a mesh, or graft, which is attached by the fastener 1 to the tissue, the maximal moment in each prong is at the line of contact along the prong where the prong passes through the slot, and not at the weaker hinge. Therefore, the force needed to bend the prongs in order to remove the fastener from the tissue is greater than the force that would have been required to bend the prongs at the hinges if the baseplate were not present. Thus, with the baseplate, the fastener is capable of withstanding forces acting on the baseplate tending to pull the fastener out of the tissue.

Figure 3:
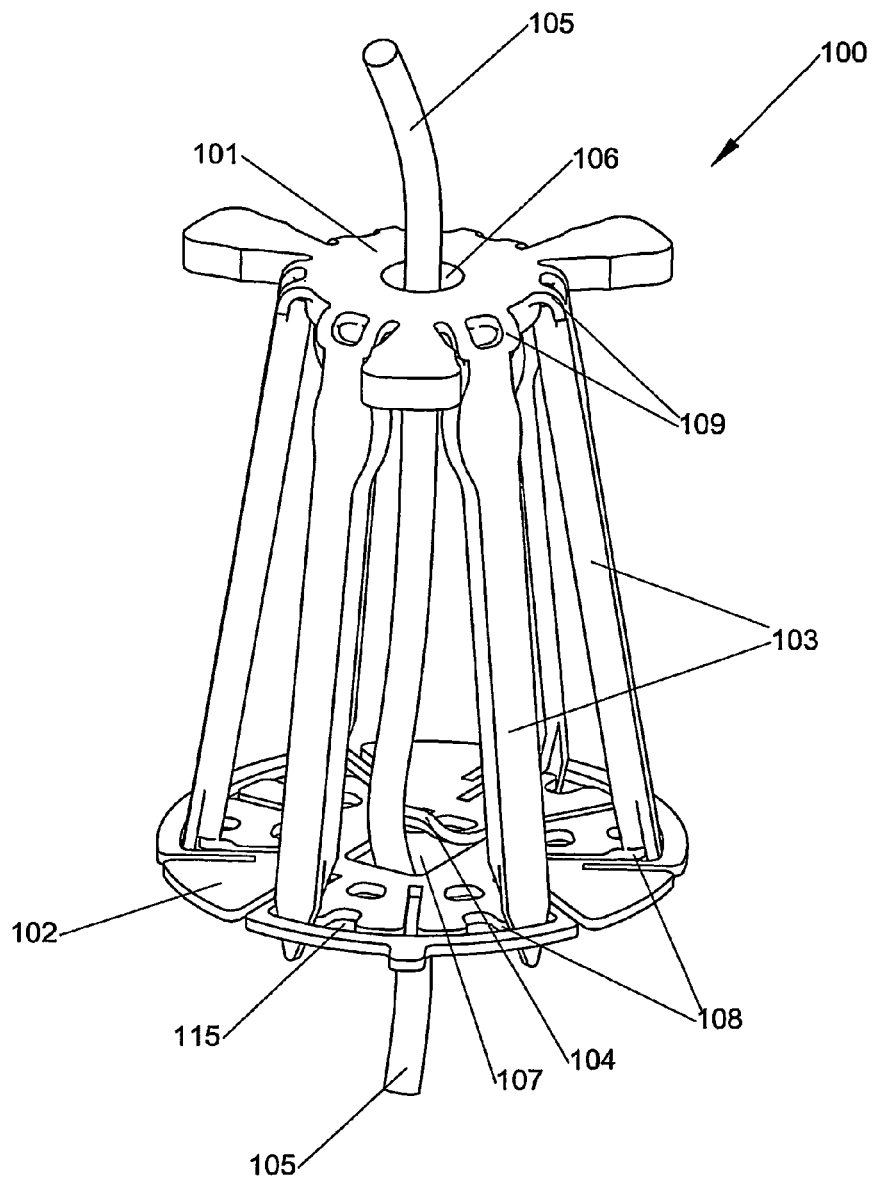
FIG. 3 shows a surgical fastener in an undeployed configuration according to another embodiment of the invention.
Figure 4:
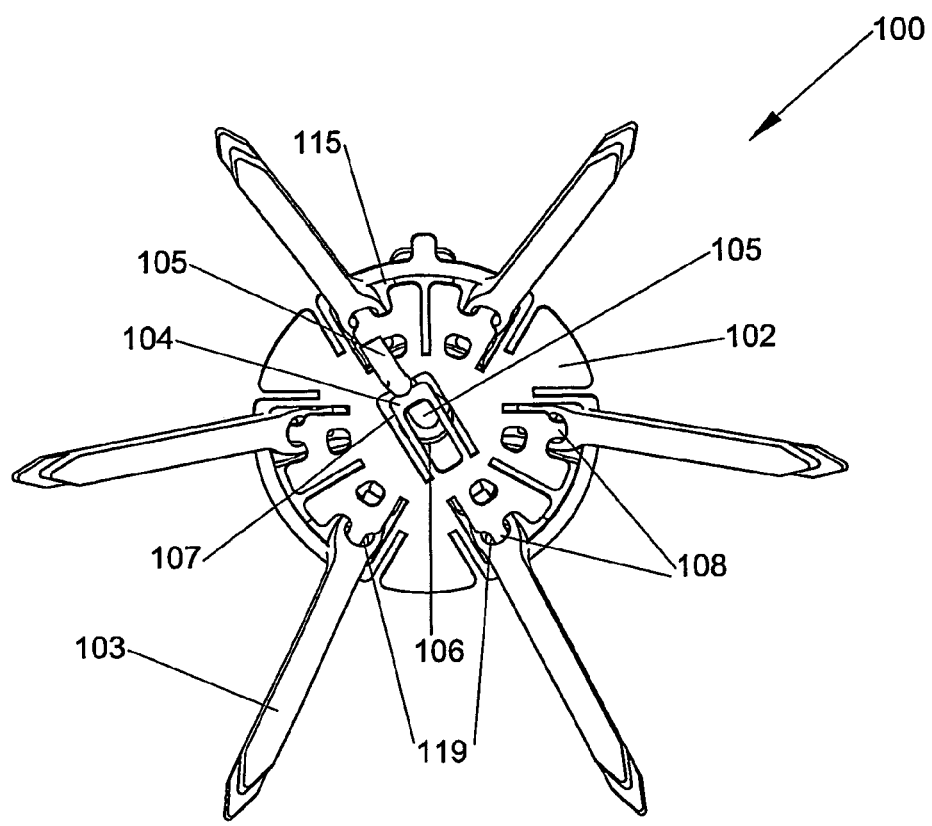
FIG. 4 shows the surgical fastener of FIG. 3 in a deployed configuration.

FIGS. 3 and 4 show a fastener 100 in accordance with another embodiment of the fastener of the invention. The fastener 100 is shown in FIG. 3 in its undeployed configuration from a side perspective view. The fastener 100 is shown in FIG. 4 in its deployed configuration from a bottom perspective view. The fastener 100 has a first element in the form of a flat crown 101. The fastener 100 also has a second element in the form of a flat baseplate 102. Two or more prongs 103 extend from the crown 101 at hinge regions 109. The baseplate 102 has a number of slots 115 through which the prongs 103 pass.

A hole 107 is provided in the baseplate 102 with a flap 104 that is initially bent out of the plane of the baseplate 102 in the undeployed configuration. A surgical filament 105 is shown passing through the hole 106 of the crown 101 and the hole 107 in the undeployed fastener. During deployment, as the crown 101 approaches the baseplate 102 the flap 104 is bent by the crown into the plane of the baseplate 102 and thus firmly grasps the filament (FIG. 4). The prongs 103 are locked in the deployed configuration by engagement of a tongue 108 extending from the baseplate 102 into each slot, 115 into an opening 119 in each prong 103.

Figure 5:
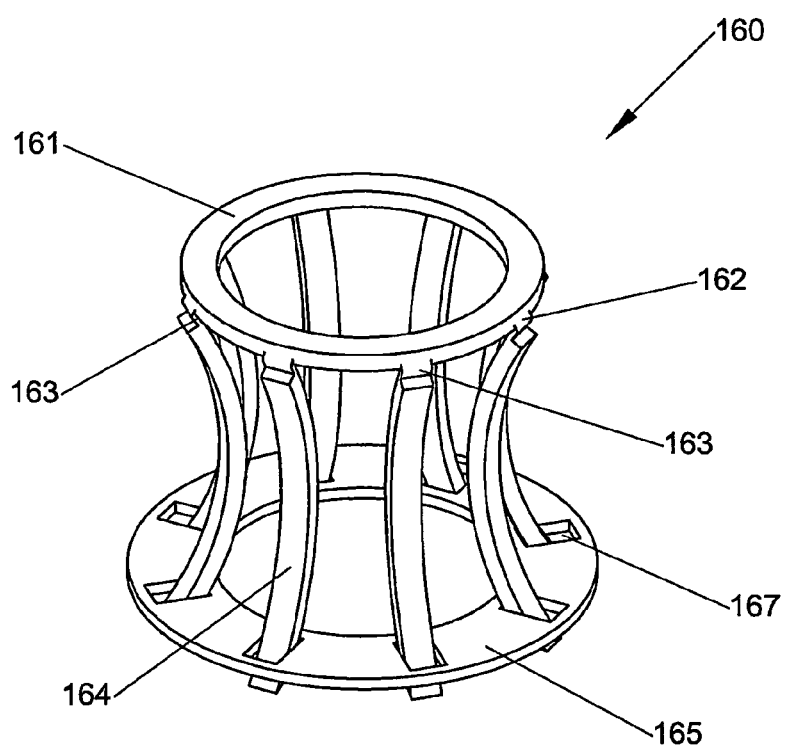
FIG. 5 shows a surgical fastener in an undeployed configuration according to another embodiment of the invention.

FIG. 5 shows a fastener 160 in its undeployed configuration in accordance with another embodiment of the fastener of the invention. The fastener 160 is shown in FIG. 5 in its undeployed configuration from a side perspective view. The fastener 160 has a first element in the form of a flat annular crown 161. The fastener 160 also has a second element in the form of a flat annular baseplate 165. Prongs 164 extend from the crown 161 at hinge regions 162. The hinges 162 are integral hinges formed by a thinned region 163 of each prong 164 at the site of connection to the crown 161. The baseplate 165 has slots 167 through which the prongs extend.

Figure 6:
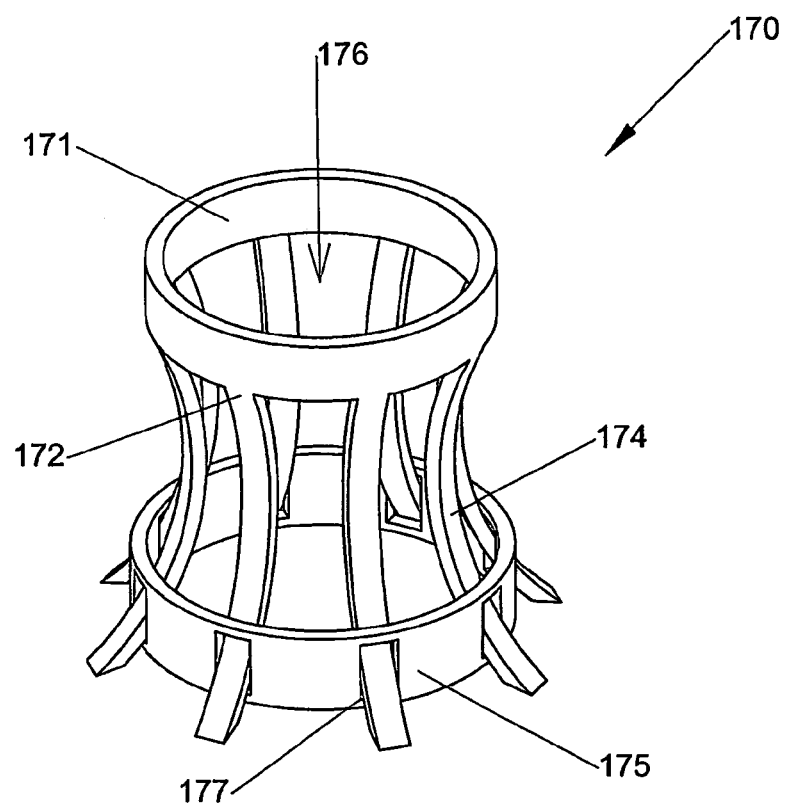
FIG. 6 shows a surgical fastener having a hollow lumen in an undeployed configuration according to another embodiment of the invention.

FIG. 6 shows a fastener 170 in its undeployed configuration in accordance with another embodiment of the fastener of the invention. The fastener 170 is shown in FIG. 6 in its undeployed configuration from a side perspective view. The fastener 170 has a first element in the form of a cylindrical crown 171. The fastener 170 also has a second element in the form of a cylindrical baseplate 175. Prongs 174 extend from the crown 171 at hinge regions 172. The baseplate 175 has slots 177 through which the prongs extend. The fastener 170 has a hollow lumen 176, and is thus adapted for deployment in a body lumen such as a blood vessel.

Figure 7:
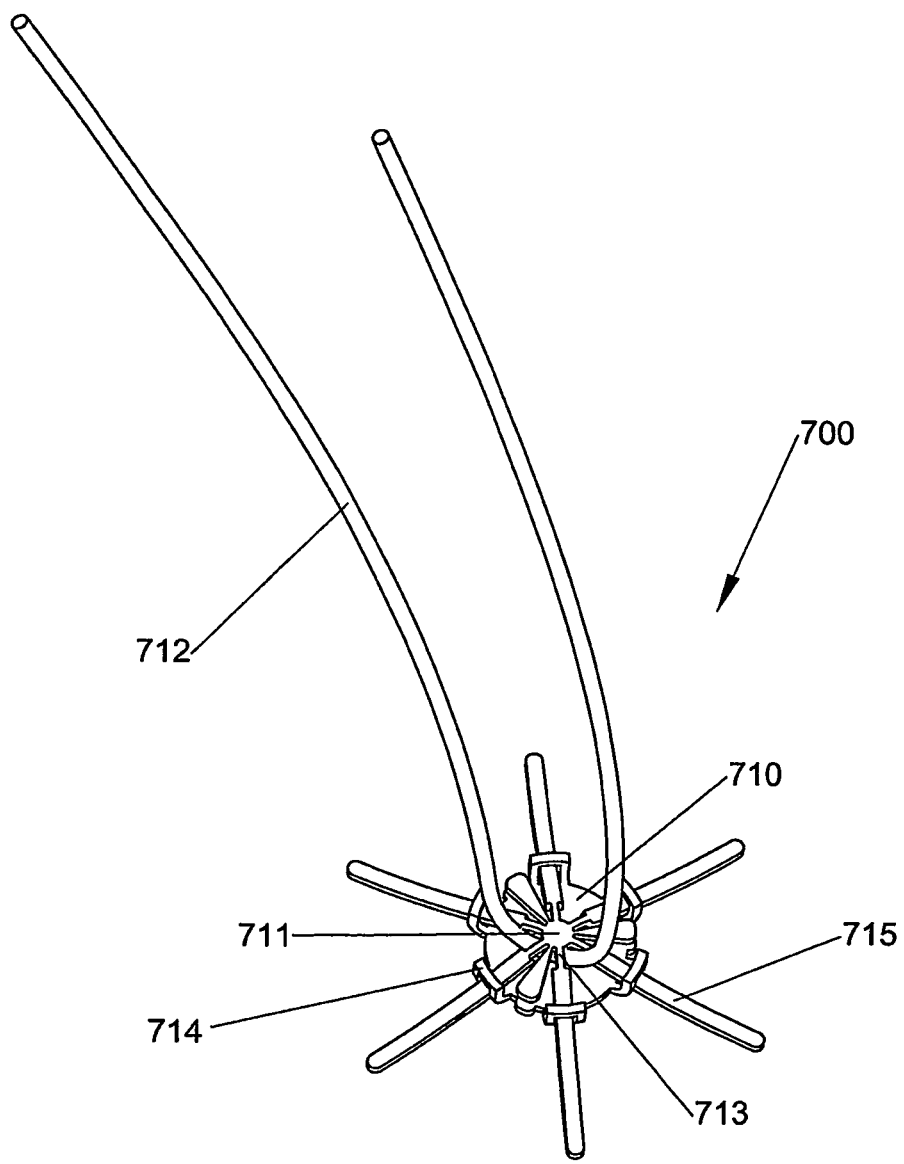
FIG. 7 shows a surgical fastener in a deployed configuration grasping a surgical filament according to another embodiment of the invention.

FIG. 7 shows a fastener 700 in its deployed configuration in accordance with another embodiment of the fastener of the invention. The fastener 700 is shown in FIG. 7 from a top perspective view. The fastener 700 has a first element in the form of a flat crown 711. The fastener 700 also has a second element in the form of a baseplate 710. Prongs 715 extend from the crown 711 at hinge regions 713 formed by a narrowed region at the connection of each prong 715 to the crown 711. A surgical filament 712 is shown in FIG. 7 grasped between the crown 711 and the baseplate 710 in the deployed fastener. The filament 712 may serve to remove the fastener from the tissue at any time after deployment. The fastener 700 is brought to its undeployed configuration by immobilizing the baseplate and pulling the filament 712 so as to pull the crown 711 away from the baseplate.

Figure 8:
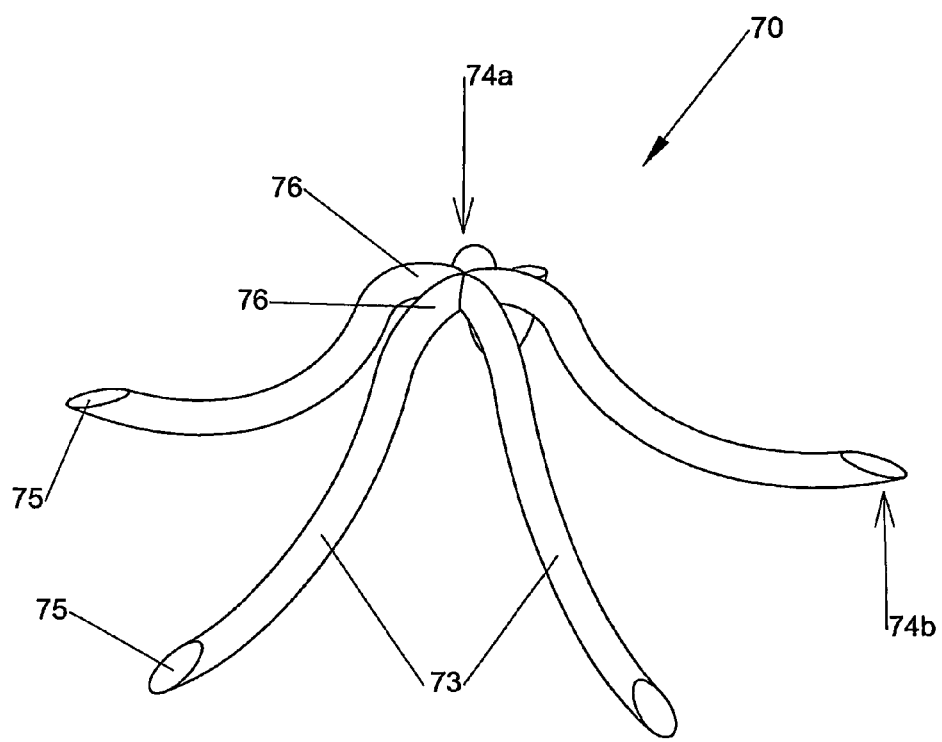
FIG. 8 shows a surgical fastener in an undeployed configuration according to another embodiment of the invention.

FIG. 8 shows a surgical fastener 70 in its undeployed configuration, in accordance with another embodiment of the invention. The fastener 70 has S shaped prongs 73 that are joined together at a common attachment site 76 that forms a crown 76. The fastener 70 does not have a baseplate. The fastener 70 is deployed by applying a normal force on the crown 76 directed towards the prong tips as indicated by the arrow 74a and a counterforce on the prong tips 75 in the opposite direction indicated by the arrow 74b. These forces generate an extending force on the prongs 73 that causes the prongs 73 to rotate at the hinge region 76 and move in a radially outward direction from the crown 76 to penetrate the body tissue, while the crown 76 remains at the surface.

Figure 9:
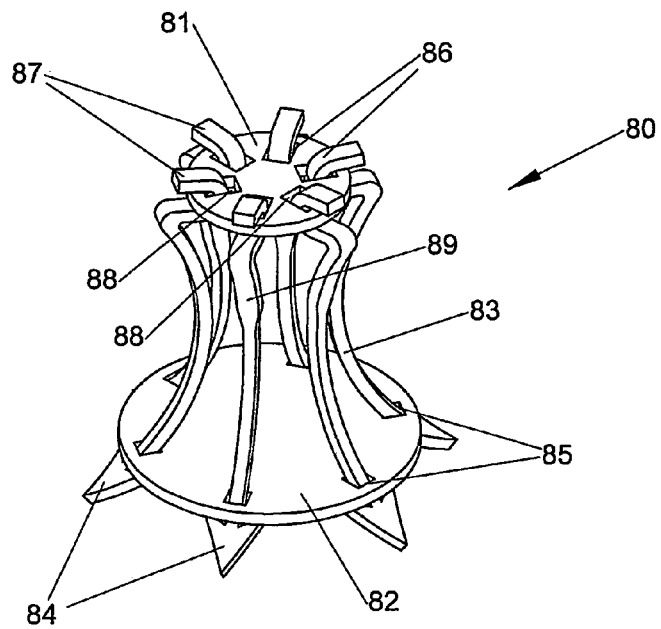
FIG. 9 shows a surgical fastener having a two-part hinge in an undeployed configuration.
Figure 10:
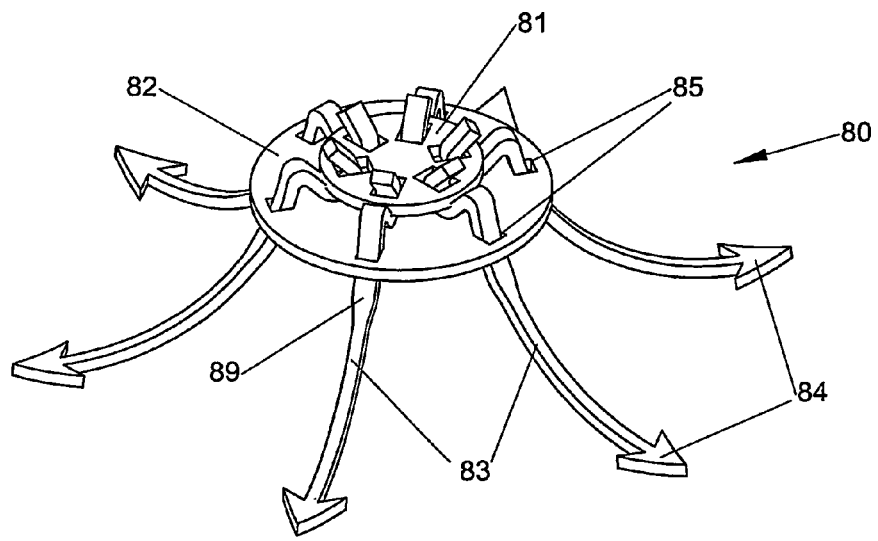
FIG. 10 shows the surgical fastener of FIG. 9 in a deployed configuration.

FIGS. 9 and 10 show a fastener 80 in accordance with another embodiment of the invention. The fastener 80 is shown in FIG. 9 in its undeployed configuration from a side perspective view. The fastener 80 is shown in FIG. 10 in its deployed configuration from a side perspective view. The fastener 80 has a first element in the form of a flat crown 81 from which extend prongs, and a second element in the form of a flat baseplate 82. Each prong 83 is joined to the crown by a hinge 86 that is not formed integrally with the crown. The hinge 86 is a two-part hinge formed by a hook 87 formed near the end of each prong that is engaged in a slot 88 in the crown. Urging the crown 81 towards the baseplate 82 causes the prongs 83 to rotate at the hinge region 86 as the prongs advance through slots 85 in the baseplate 82 and the fastener achieves its deployed configuration with the prongs extending radially outwards as shown in FIG. 10. The fastener is locked in the deployed configuration due to jamming of a widened portion 89 of the prongs 83 near the crown 81 in the slots 85.

The length of the prongs of the fastener of the invention may vary. The shape of the prongs may be straight, for example, as shown in FIG. 3. The prongs may be curved with uniform curvature as shown in FIG. 1, or may have a variable radius of curvature as shown in FIG. 8. The profile of the prong may be round, elliptic, rectangular, triangular, or any other shape and may even vary along its length. The tip of prong may be blunt, for example, as shown in FIGS. 1 and 2, pointed (FIG. 11) and/or provided with barbs 84 for better anchoring in tissue (FIG. 9).

Figure 11:
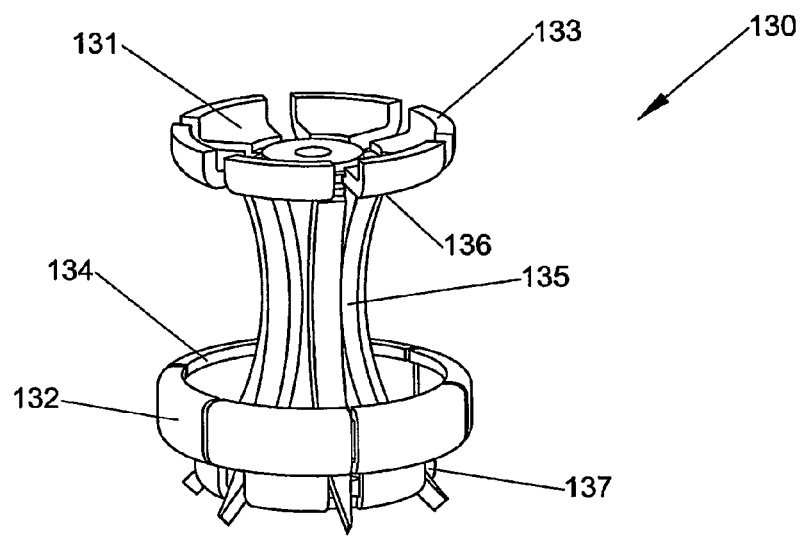
FIG. 11 shows a surgical fastener according to yet another embodiment of the invention.
Figure 12:
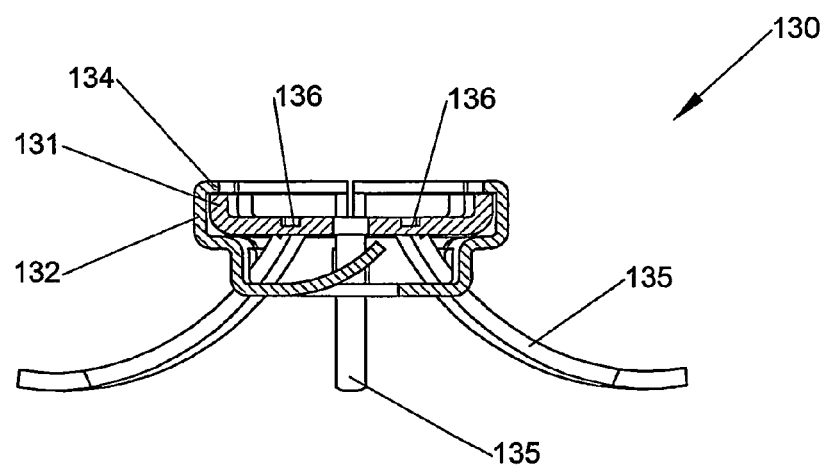
FIG. 12 shows the surgical fastener of FIG. 11 in a deployed configuration in which the fastener is locked by an engagement between the first and second elements.

FIGS. 11 and 12 show a fastener 130 in accordance with another embodiment of the fastener of the invention. The fastener 130 is shown in FIG. 11 in its undeployed configuration from a side perspective view. The fastener 130 is shown in FIG. 12 in its deployed configuration in a cross sectional view. The fastener 130 has a first element in the form of a crown 131 having a folded up lip 133. The fastener 130 also has a second element in the form of a baseplate 132 having a folded up lip 134. Prongs 135 extend from the crown 131 at hinge regions 136. The baseplate 132 has a number of slots 137 through which the prongs 135 pass.

The fastener 130 is locked in the deployed configuration by snapping of the crown 131 beneath the lip 134 of the baseplate 132, as shown in FIG. 12.

Figure 13:
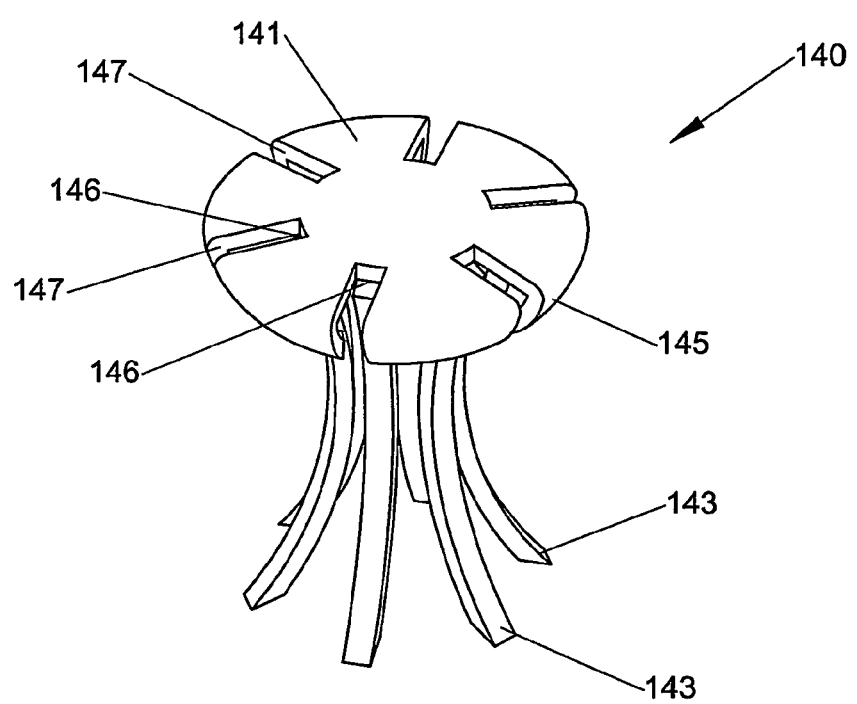
FIG. 13 shows a surgical fastener according to yet another embodiment of the invention.
Figure 14:
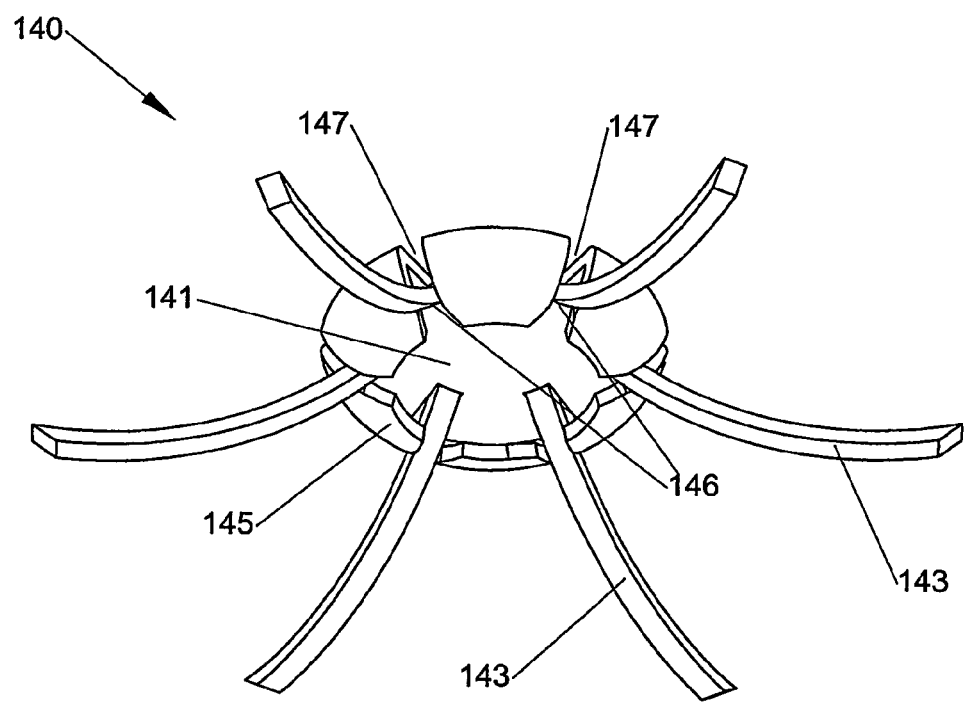
FIG. 14 shows the surgical fastener of FIG. 13 in a deployed configuration in which the fastener is locked by an engagement between the prongs and the first element.

FIGS. 13 and 14 show a fastener 140 in accordance with another embodiment of the fastener of the invention. The fastener 140 is shown in FIG. 13 in its undeployed configuration from a side perspective view. The fastener 140 is shown in FIG. 14 in its deployed configuration from a bottom perspective view. The fastener 140 has a circular crown 141 having a folded down lip 145 along its edge, but does not have a baseplate. Prongs 143 extend from the crown 141 at hinge regions 146. Radial slots 147 in the lip 145 of the crown 141 are trapezoidal in shape being wider nearer to the edge of the lip 145. During deployment, the prongs 143, rotate outwardly about the hinge regions 146, and become jammed in the narrower section of the radial slots 147, so as to lock the fastener 140 in its deployed configuration.

Figure 15:
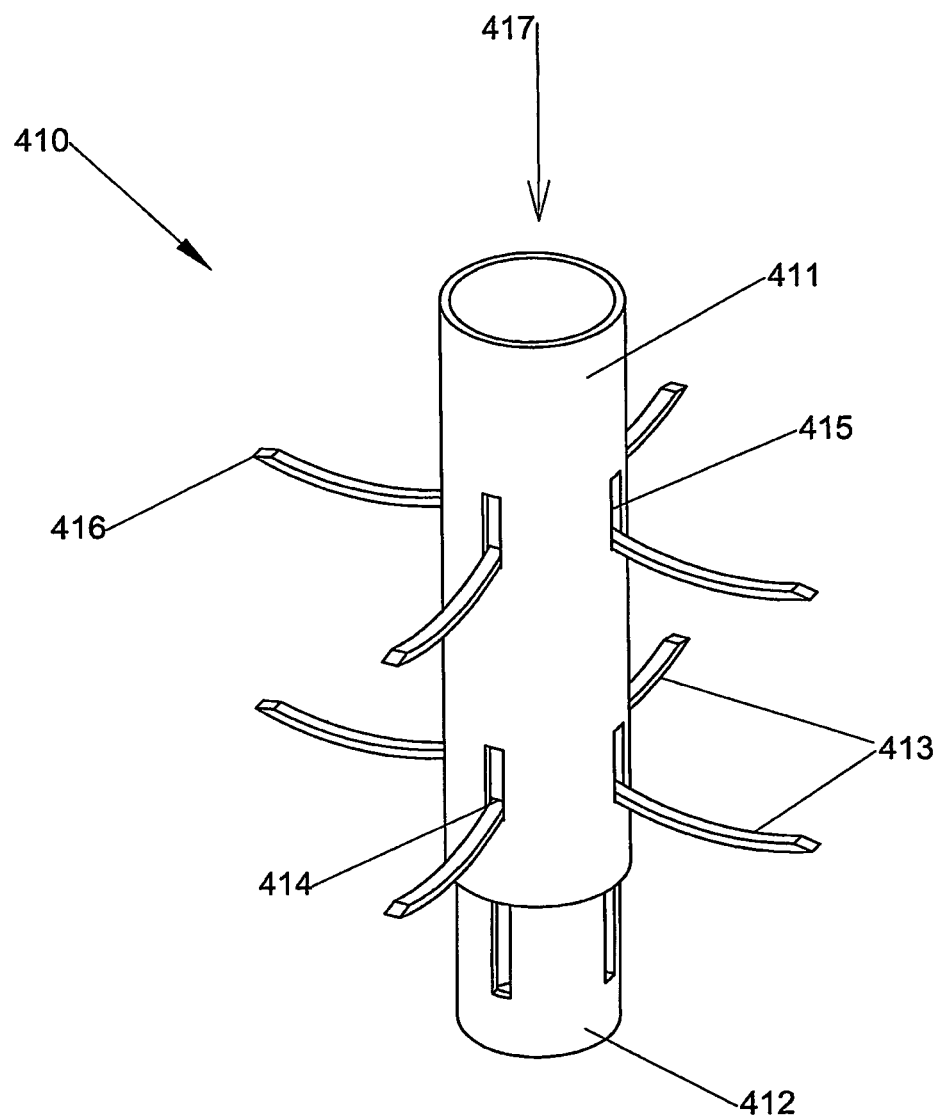
FIG. 15 shows a surgical fastener according to an embodiment of the invention in which the first and second elements are coaxial cylinders.

FIG. 15 shows a fastener 410 in accordance with another embodiment of the fastener of the invention. The fastener 410 has a first element 412 in the form of a cylinder, to which prongs 413 are attached by hinges 414. The first element 412 is situated within a second element 411 in the form of a coaxial external cylindrical sleeve 411. The prong tips 416 pass through slots 415 in the wall on the external sleeve 411. An axial movement of the inner sleeve 412 relative to the external sleeve 411 in the direction of the arrow 417 exerts a force on the prongs and causes them to rotate at the hinges 414 and extend radially outwardly, to penetrate surrounding structures or tissues.

Figures 16A, 16B:
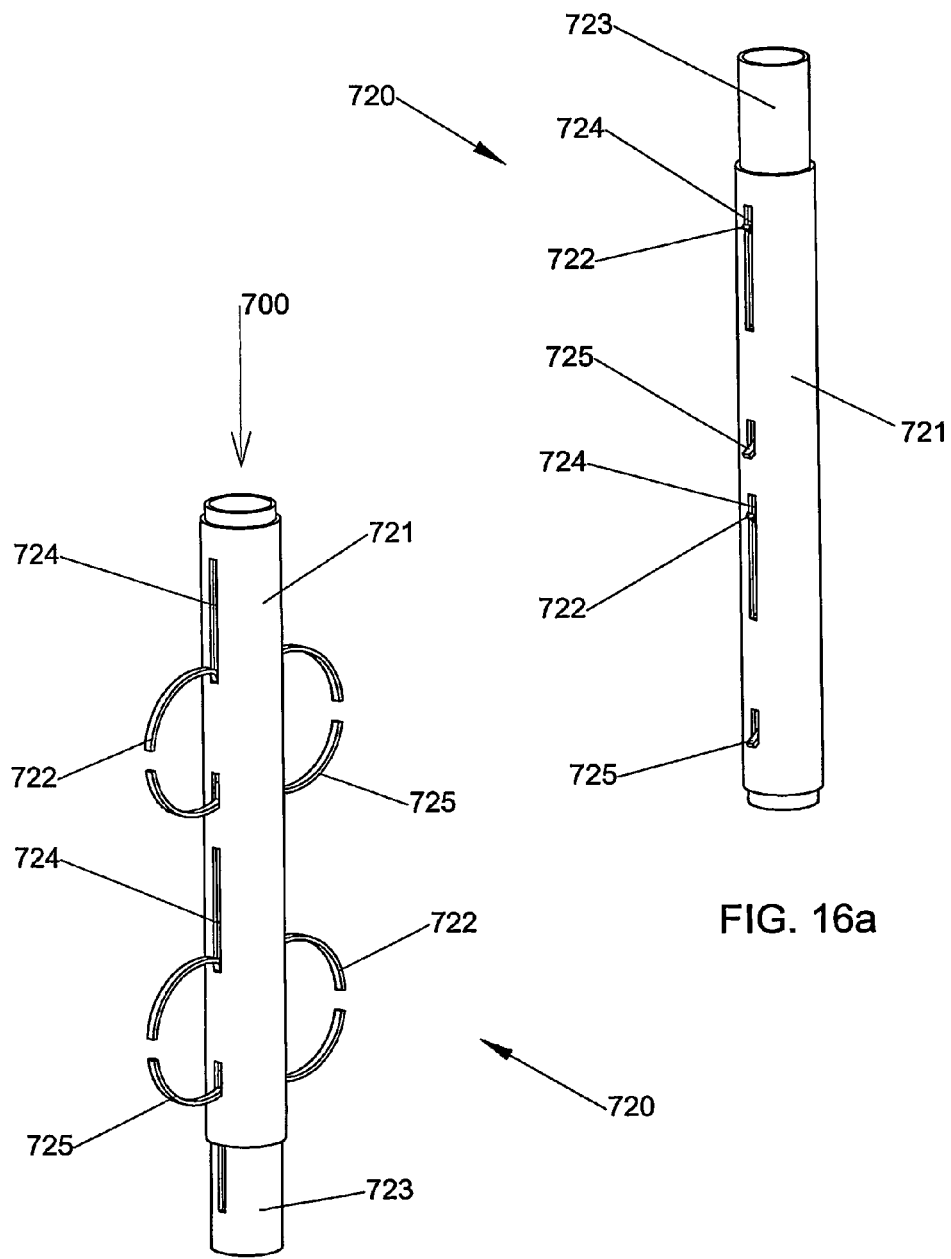
FIG. 16 shows a surgical fastener according to another embodiment of the invention in which the first and second elements are coaxial cylinders and the second element is provided with prongs.

FIG. 16a and FIG. 16b show another embodiment 720 in which the first and second elements are in the form of an inner sleeve 723 and an outer sleeve 721, respectively. The outer sleeve is also provided with one or more rows of prongs 722.

FIG. 16a shows the fastener in the undeployed state and FIG. 16b shows the fastener in the deployed state. The prongs 722 of the outer sleeve 721 are oriented in proximity to slots 724 of the inner sleeve. When sliding the inner sleeve 723 axially, relative to the outer sleeve, in the direction of the arrow 700 the slots 724 of the inner sleeve 724 exert a force on the prongs of the outer sleeve, forcing them to extend outwardly and acquire the deployed state (FIG. 16b). However, since the force exerted on the prongs 725 of the inner sleeve 723 is in the opposite direction to the force exerted on the prongs 722 of the outer sleeve, the prongs of the outer sleeve and those of the inner sleeve extend with oppositely directed curvature. This provides better gripping of the surrounding structures and/or tissues. Locking of the fastener in the deployed state may be by the engagement of the prongs with the slots' edges or by any other of the locking means previously mentioned.

Figure 17:
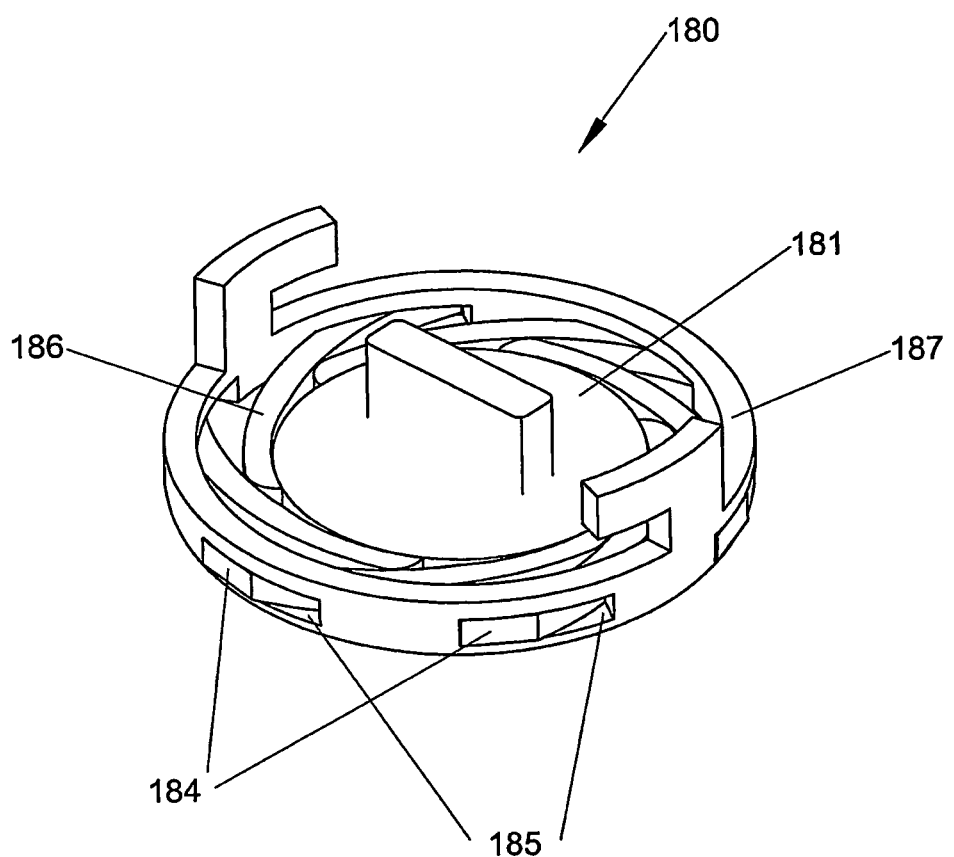
FIG. 17 shows a surgical fastener in an undeployed configuration according to another embodiment of the invention in which the first element is a disk that rotates relative to the second element.
Figure 18:
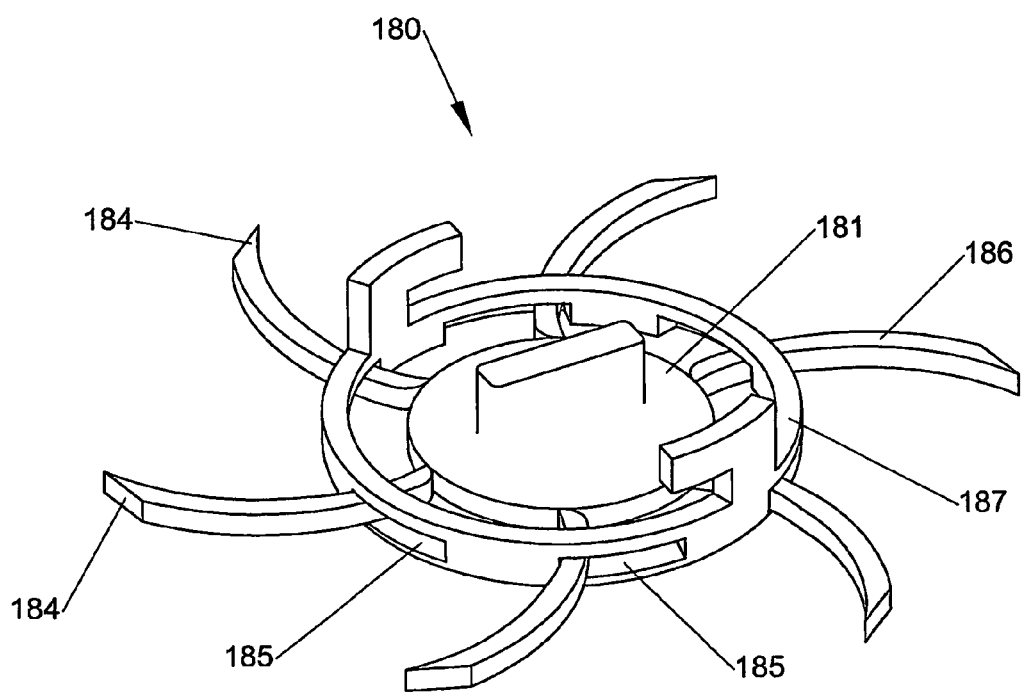
FIG. 18 shows the surgical fastener of FIG. 17 in a deployed configuration.

FIGS. 17 and 18 show a surgical fastener 180 in accordance with yet another embodiment of the invention. The fastener 180 is shown in its undeployed configuration in FIG. 17 and in its deployed configuration in FIG. 18. The fastener 180 has a first element 181 in the form of a disk from which extend prongs 186. The second element is in the form of an outer sleeve 187 provided with slots 185, through which prong tips 184, pass in the undeployed state. The fastener 180 is deployed by rotating the first element 181 inside the second element 187. As the first element 181 is rotated, the slot edges exert a force on the prongs and cause them to splay radially outward through the slots 185 so as to penetrate the surrounding structures and/or tissues.

Locking of the fastener of FIGS. 17 and 18 in the deployed configuration results from the fact that the force applied on the prongs in order to detach the fastener from the tissue is perpendicular to force necessary to bend the prongs to it's deployed configuration. Therefore, a moment directed to detach the fastener will not be applied at the hinges in the same way as the deployment moment, but at a much stronger region of the prongs resulting in locking the fastener in the deployed configuration. In this case the fastener may also be provided with one or more rows of prongs. The fastener may be attached to a thread or filament and may serve as an anchor.

Figure 19:
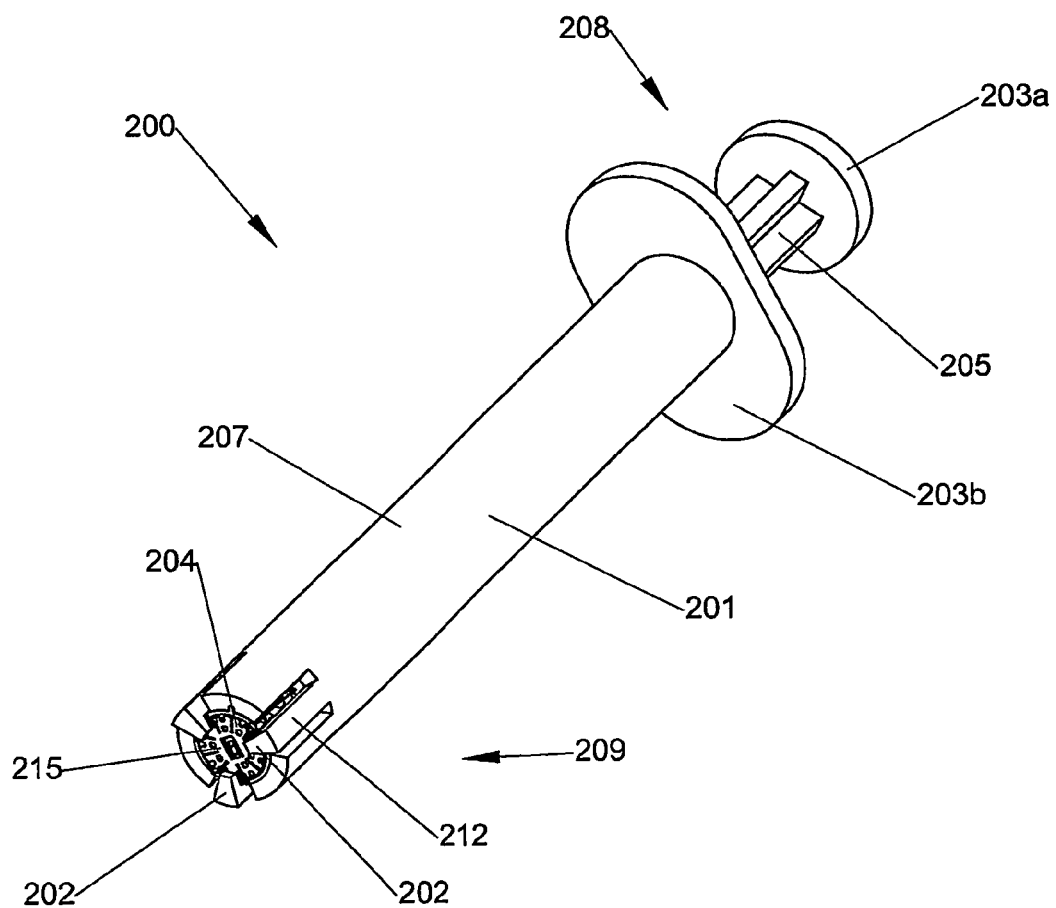
FIG. 19 shows a surgical fastening in a perspective view device in accordance with embodiment of the invention.
Figure 20A:
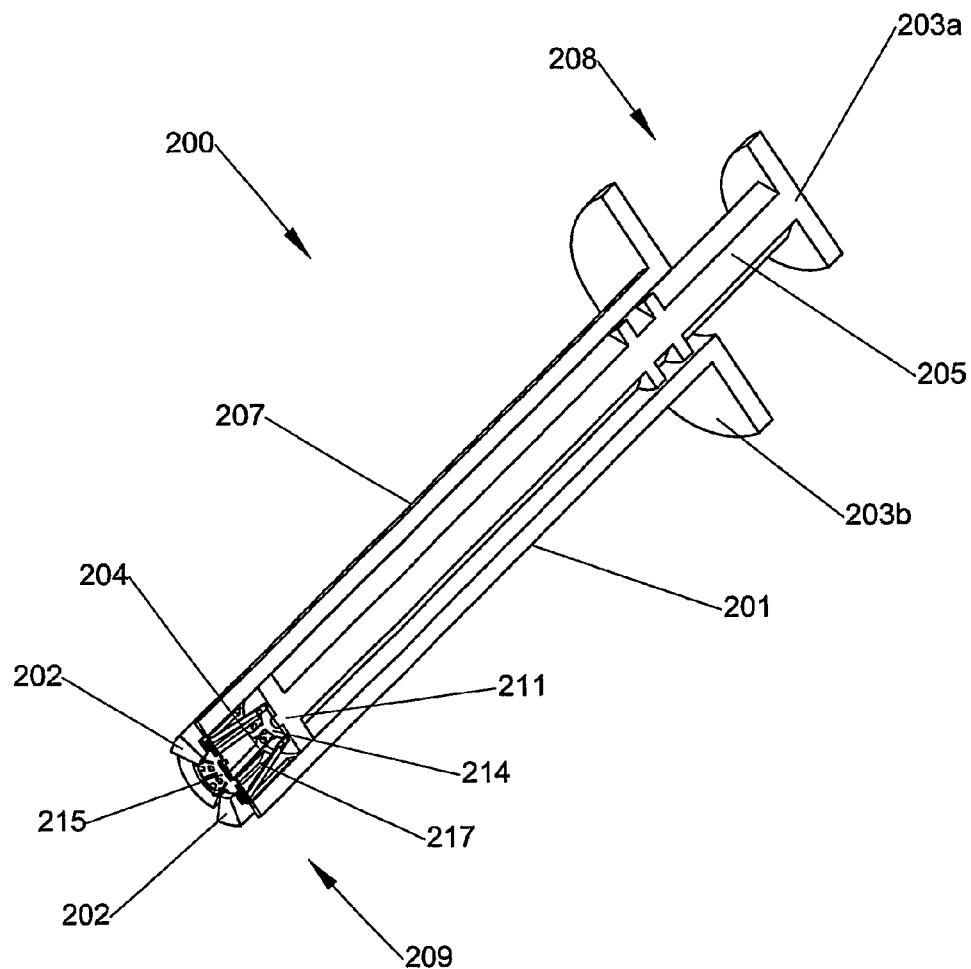
FIG. 20 shows the surgical fastening device of FIG. 19 in a longitudinal sectional view during deployment of a surgical fastener.

FIGS. 19 and 20 show a surgical fastening device 200 in accordance with one embodiment of this aspect of the invention. The fastening device 200 is shown in FIG. 19 in perspective view and in FIG. 20 in longitudinal section. The fastening device 200 is used to deploy a surgical fastener 204 of the invention having a crown 214 and baseplate 215, such as the fastener 100 shown in FIGS. 3 and 4. The fastening device 200 is provided with a slender shaft 207 having a proximal end 208 and a distal end 209. The shaft 207 has a cylindrical sleeve 201 and a plunger 205. The distal end of the sleeve is provided with one or more stops 202 projecting radially inwards toward the longitudinal axis of the sleeve. Each stop 202 is located at the end of a projection 212 cut in the wall of the sleeve 201. As shown in FIGS. 19 and 20a, the sleeve houses a single fastener 204 in its undeployed configuration at the distal end of the sleeve 201 between the stops 202 and a ramming head 211 located at the distal end of the plunger 205.

Figure 20B:
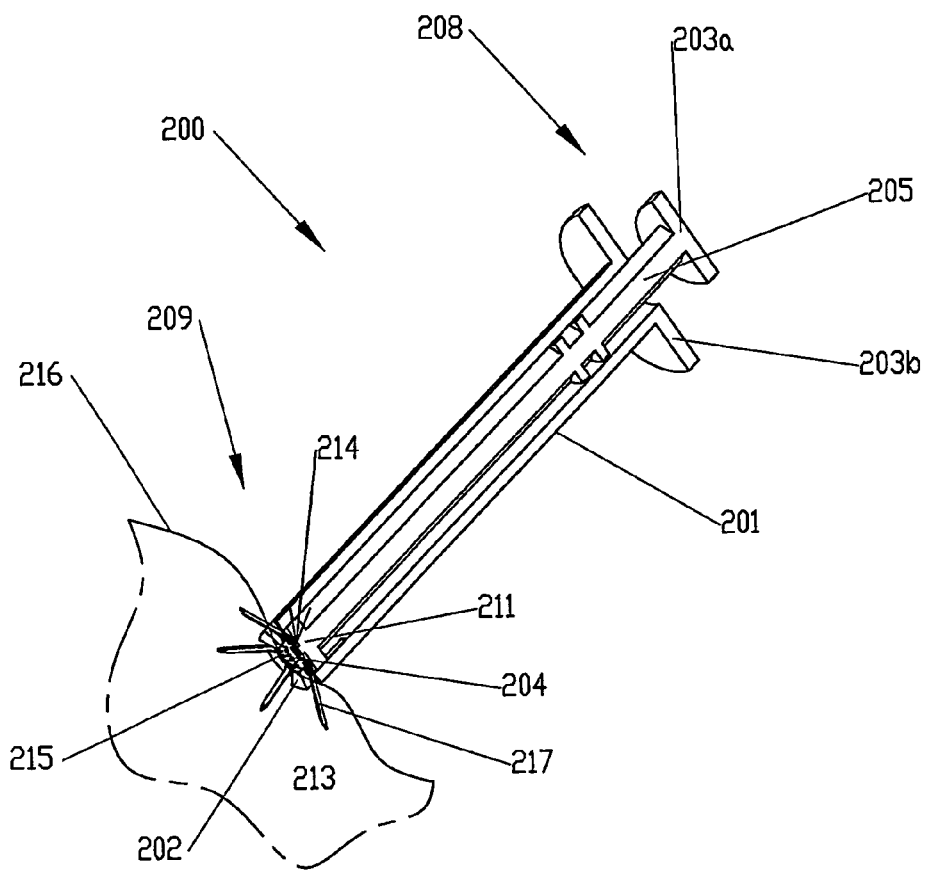
Figure 20C:
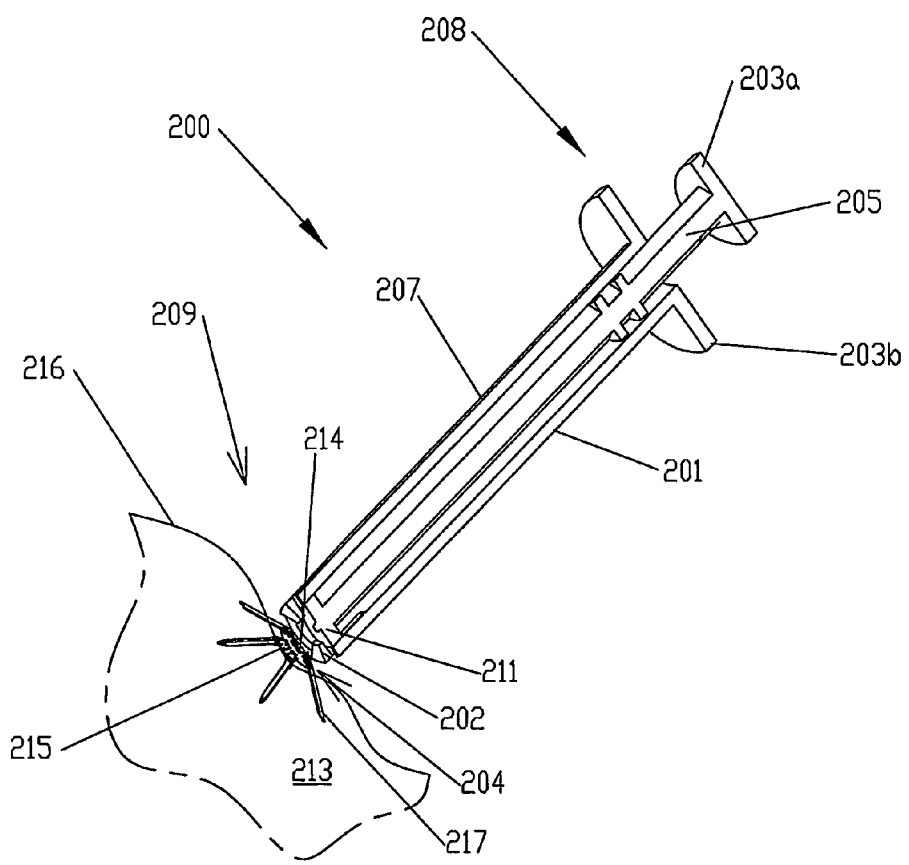

As shown in FIG. 20b, the distal end 209 of the fastener 200 is delivered to a surface 216 of a tissue 213 where the fastener 204 is to be deployed. The fastener 204 is then deployed by depressing the plunger 205 distally within the sleeve 201. This is facilitated by pressing a knob 203a located on the proximal end of the plunger 205 against a flange 203b on the proximal end of the sleeve 201. As the ramming head 211 presses on the crown 214 of the fastener 204, the stops 202 provide a counter-pressure on the baseplate 215 so as to create axial compression of the fastener 204, causing the prongs 217 of the fastener to splay radially outward into the tissue 213 as the fastener 204 attains its deployed configuration. The prong tips develop a curved trajectory as they penetrate into the tissue to a specific predetermined depth and then move laterally, similar to the trajectory of a curved suturing needle within a tissue. The force necessary to fully spread the prongs 217 and deploy the fastener 204 is developed within the fastening device 200 between the ramming head 211 and the stops 202 and is not applied to the tissue, thus preventing damage to the tissue such as tearing or perforating. The prongs of the fastener penetrate the tissue smoothly and attach the fastener to the tissue. As shown in FIG. 20c, after deployment of the fastener 204, the fastener 204 is released from the fastening device 200 by transiently displacing the stops 202 radially outward. For example, the stops 202 may move radially outward and release the fastener when a force is applied to the crown 214 by the ramming head 211 that forces the baseplate 215 to pass the stops 202, by overcoming the elasticity of the projections 212. The force for releasing the fastener is greater than the force required for bringing the fastener to its deployed configuration. After the baseplate 215 has passed the stops 202, the stops 202 return to their initial location under the influence of the elasticity of the projections 212. After deployment, the crown 214 and the baseplate 215 of the fastener 204 are attached to the surface 216 of the tissue 213, and do not penetrate into the tissue. The fastening device 200 can then be removed from the body.

Figure 21A:
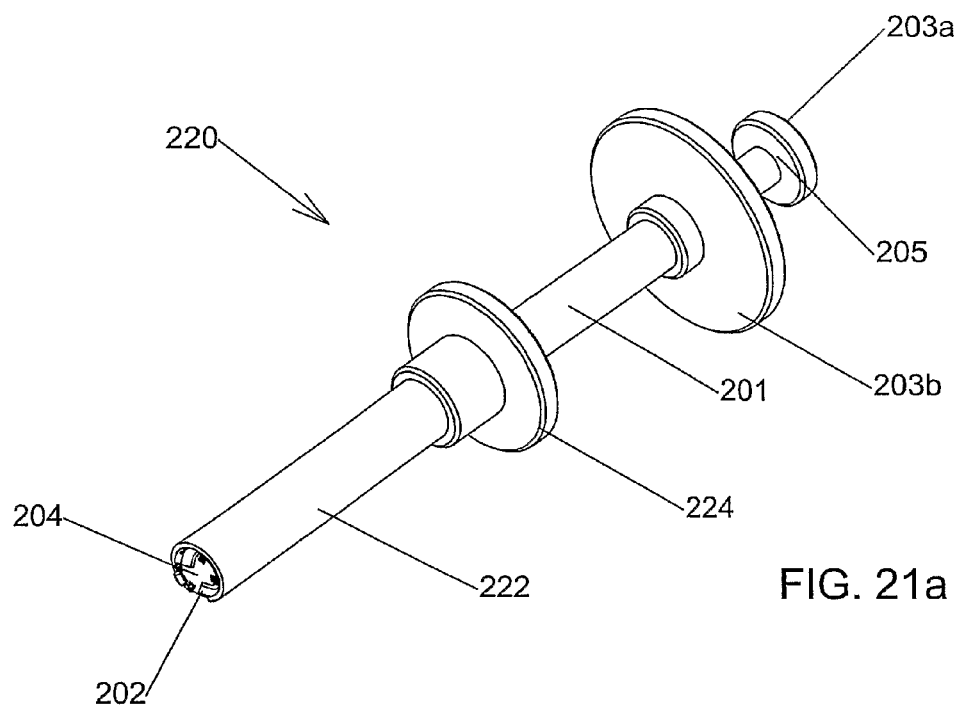
FIG. 21 shows a surgical fastening device in accordance with another embodiment of the invention.
Figure 21B:
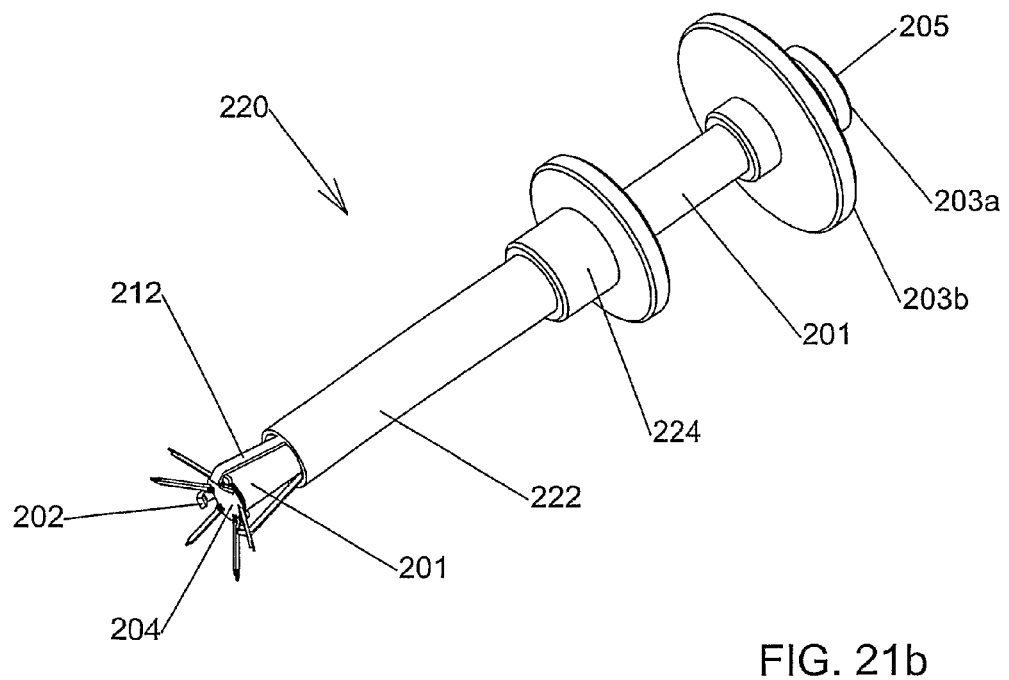

FIG. 21 shows a second embodiment 220 of the fastening device of the invention. The fastening device 220 has several elements in common with the fastening device 200 described above in reference to FIGS. 19 and 20, and these elements are indicated by the same reference numerals in FIG. 21 as was used in FIGS. 19 and 20 without further comment. The shaft of the fastening device 220 includes an external sheath 222 that is coaxial with the sleeve 201. As shown in FIG. 21a, during deployment of the fastener 204, the external sheath 222 is in a first position relative to the sleeve 201 in which it surrounds the distal end of the sleeve 201, so that the stops 202 are prevented from moving radially outward during deployment of the fastener 204. As shown in FIG. 21b, after deployment of the fastener, the sheath 222 is retracted in a proximal direction by pulling on a knob 224 to expose the distal end of the sleeve 201. The stops 202 are no longer constrained in this position and move radially outward and thus release the fastener 204. The outward movement of the stops 202 may be, for example, under the influence of the elasticity of the projections 212 or by being pushed out by the ramming head 211 as explained above in reference to FIGS. 19 and 20. Alternatively, the projections 212 may be floppy.

Figure 22:
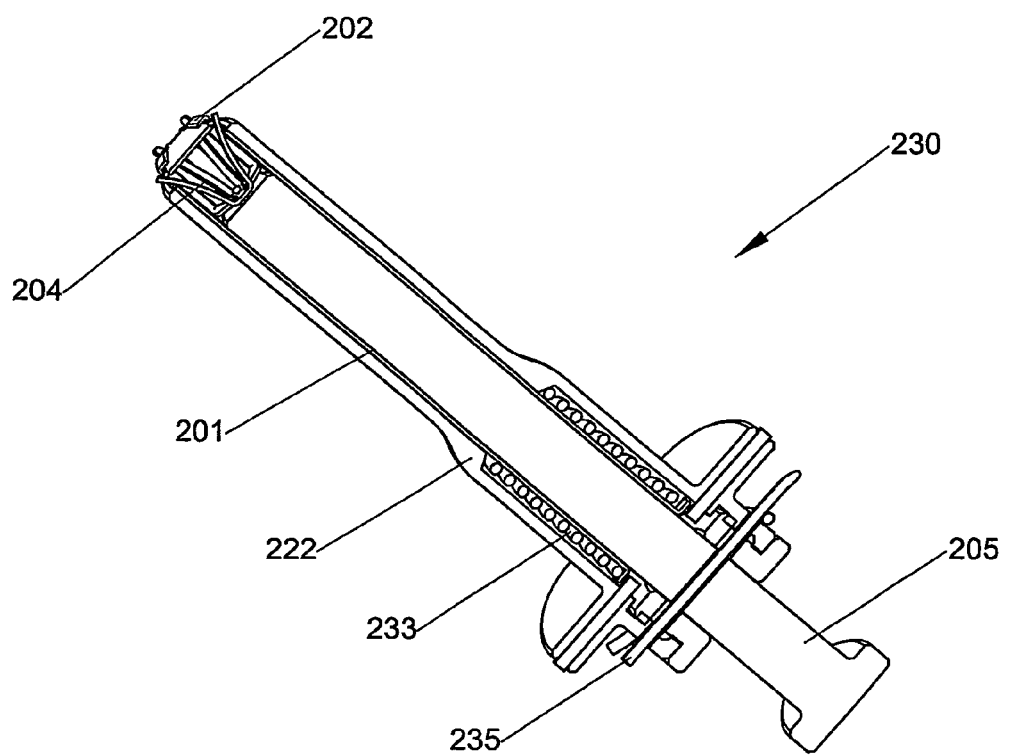
FIG. 22 shows a surgical fastening device in accordance with another embodiment of the invention.
Figure 23:
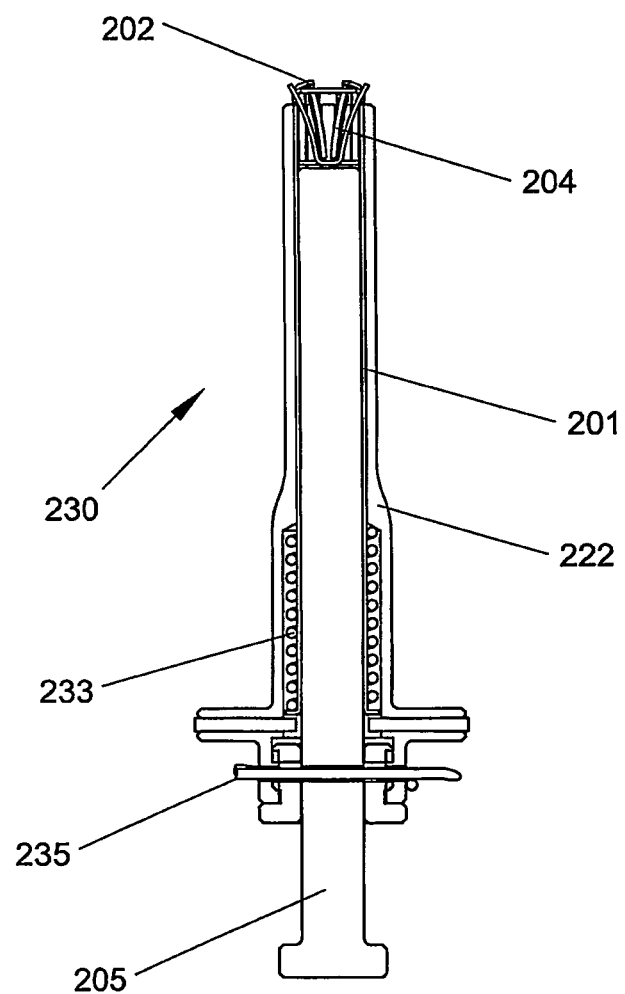
FIG. 23 shows the surgical fastening device of FIG. 22 in a longitudinal sectional view.
Figure 24:
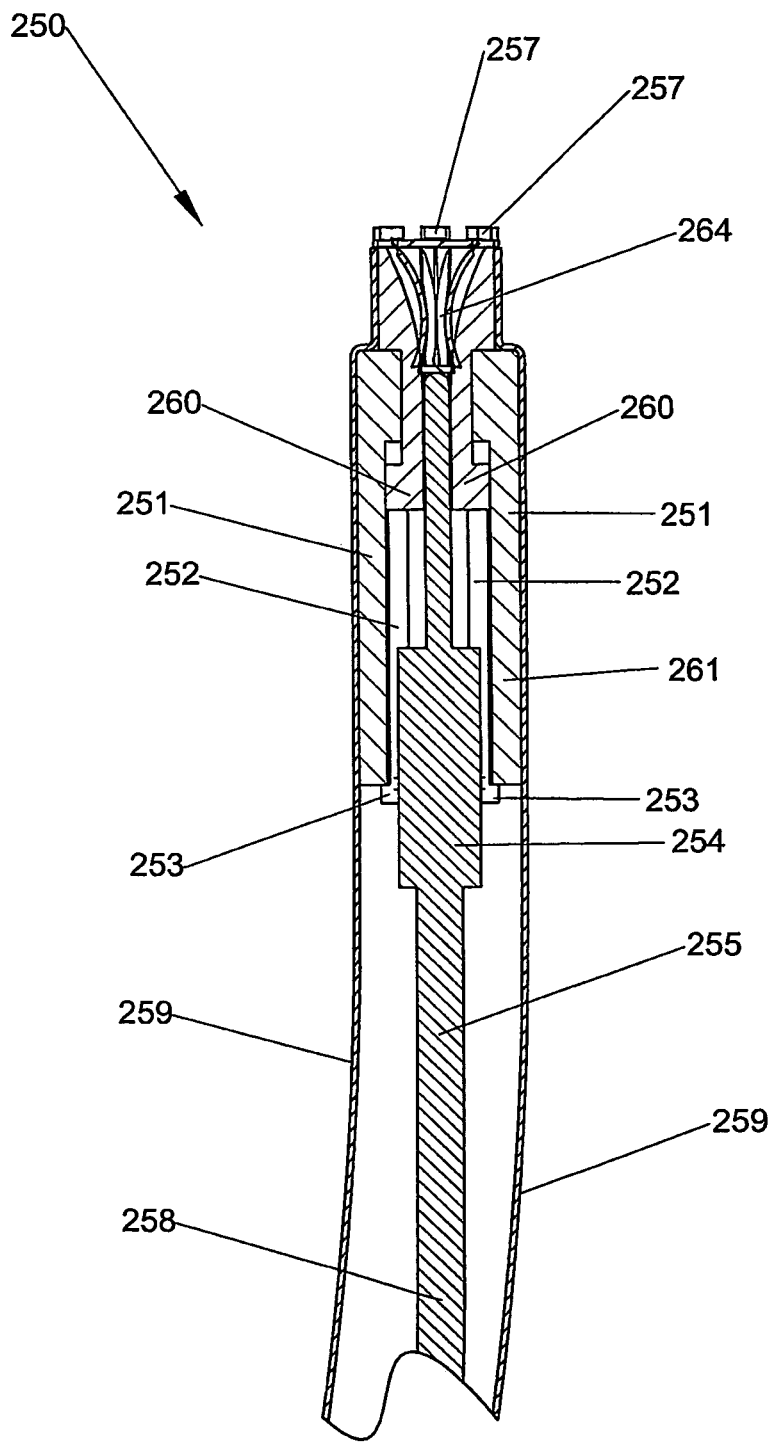
FIG. 24 shows a surgical fastening device having a curved shaft prior to deployment of a surgical fastener in accordance with another embodiment of the invention.

FIGS. 22 and 23 show a second embodiment 230 of the fastening device of the invention. The fastening device 230 has several elements in common with the fastening device 220 described above in reference to FIG. 21, and these elements are indicated by the same reference numerals in FIGS. 22 and 23 as was used in FIG. 21 without further comment. In the fastening device 230, the sheath 222 and the sleeve 201 are engaged by a connecting spring 233 that is pre-compressed to withstand a force greater than the force necessary to compress the fastener into its deployed configuration. After compressing the fastener to its deployed configuration, a force that exceeds the pre-compressed force of the spring 233 is applied to the sleeve 201 so as to further compress the spring 233. The sleeve 201 advances and extends beyond the distal end of the sheath 222, and the stops 202 move outward, no longer being constrained by the sheath 222, thus releasing the deployed fastener 204. In order to prevent inadvertent actuation of the fastening device, a safety pin 235 may be provided that has to be removed before use.

Figure 25:
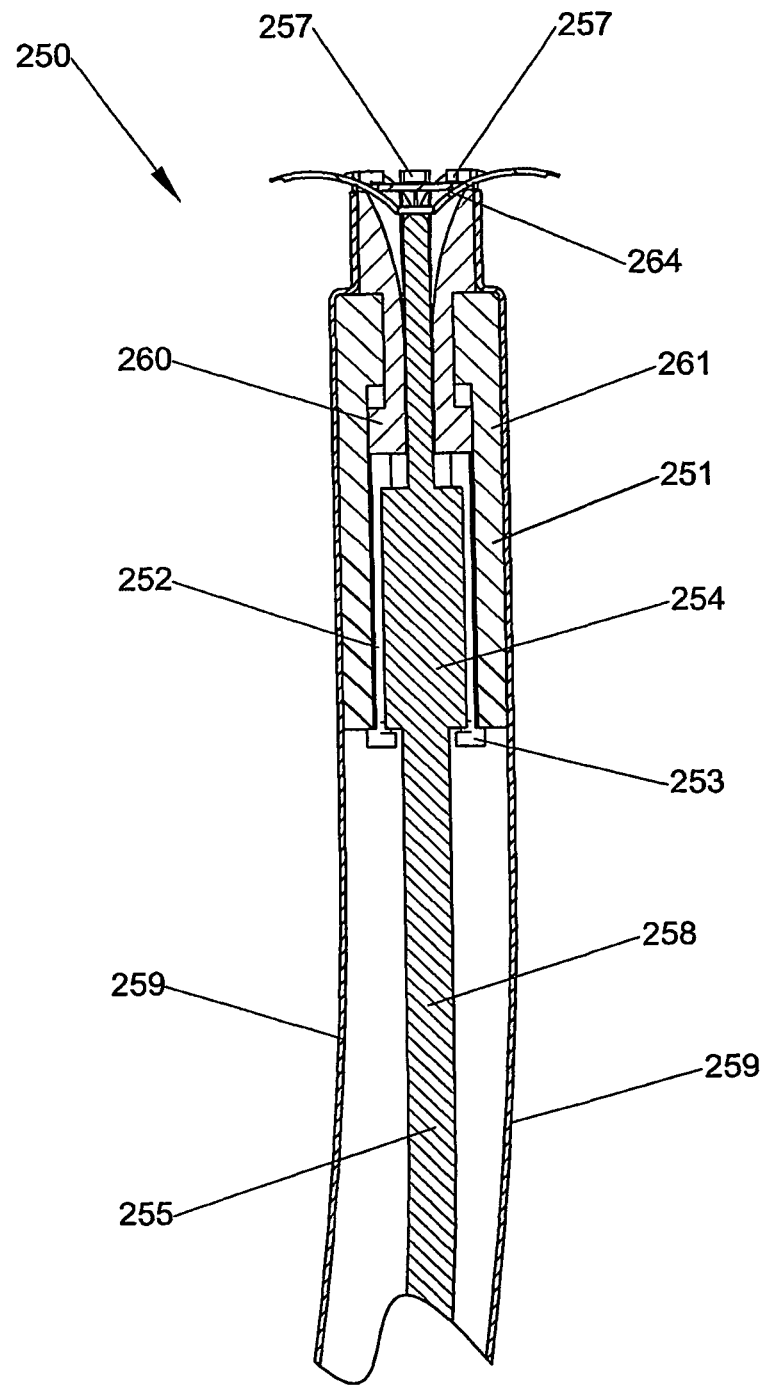
FIG. 25 shows the surgical fastening device of FIG. 24 during deployment of a surgical fastener.
Figure 26B:
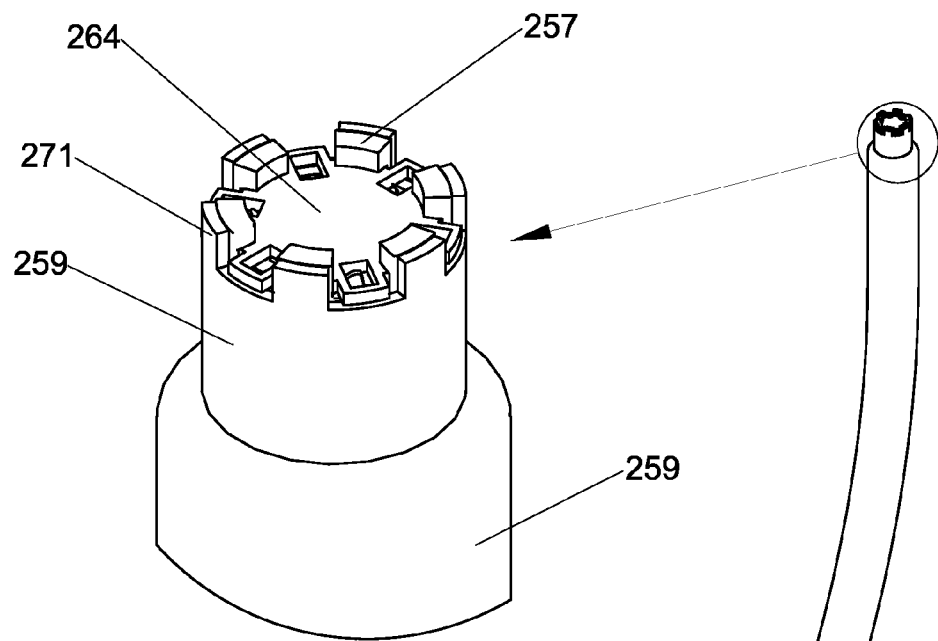
FIGS. 26a and 26b show perspective views of the surgical fastening device of FIGS. 24 and 25 and an enlargement of the distal end shown in FIG. 26a, respectively.
Figure 26A:
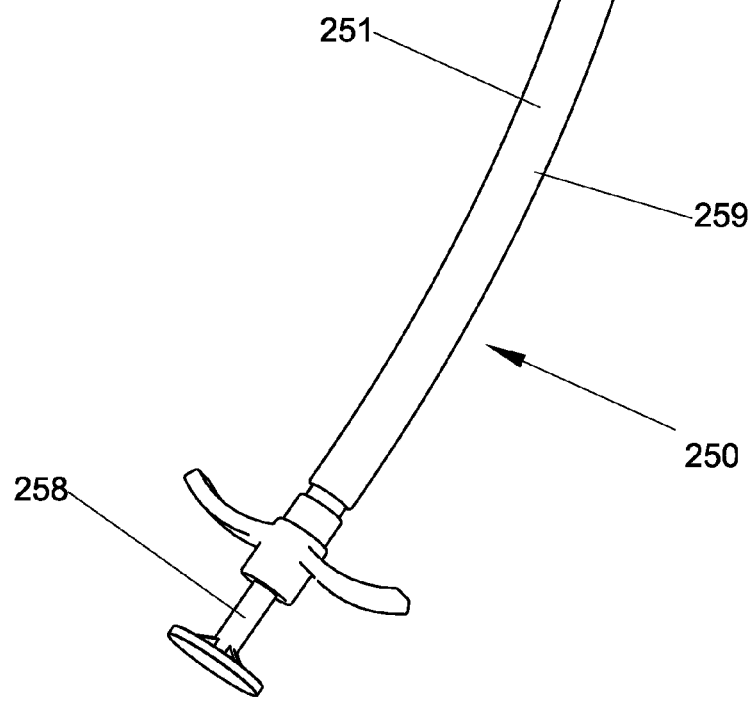

Another embodiment 250 of the fastening device of the invention shown in FIGS. 24, 25 and 26a-26b, has a curved sheath 251 surrounded by a tube 259. Longitudinal projections 252 extend from an annular ring 260. Each projection 252 engages, via a radial protrusion 253 extending from the projection 252 towards a depression within the sheath 251. A tube 261 is attached to the inner surface of the surrounding tube 259. A plunger 258 has a first segment 254 with a large diameter profile 254 and a more proximally segment 255 having a narrower profile. The protrusions 253 of the projections 252 are forced outwardly within the depressions of the tube 261 by the distal larger diameter segment 254 of the plunger 258. During deployment of the fastener 264, the plunger 258 moves distally relative to the surrounding tube 259 and the tube 261, thus compressing the fastener 264. As the plunger 258 advances distally the narrower profile 255 of the plunger 258 becomes situated in proximity to the protrusions 253, as shown in FIG. 25. The constraint previously imposed on the protrusions 253 by the wide segment 254 of the plunger 258 is thus relieved, and the protrusions 253 can then move medially and leave the tube 261. Depressing the plunger 258 further advances the plunger within the sheath and transmits a force to a complex consisting of the annular ring 260, the longitudinal projections 252, the protrusions 253 and the stops 257. The force applied to the stops allows advancement of the complex in relation to the sheath tips 271. The unconstrained stops 257 then release the fastener 264, as explained above.

Figure 27:
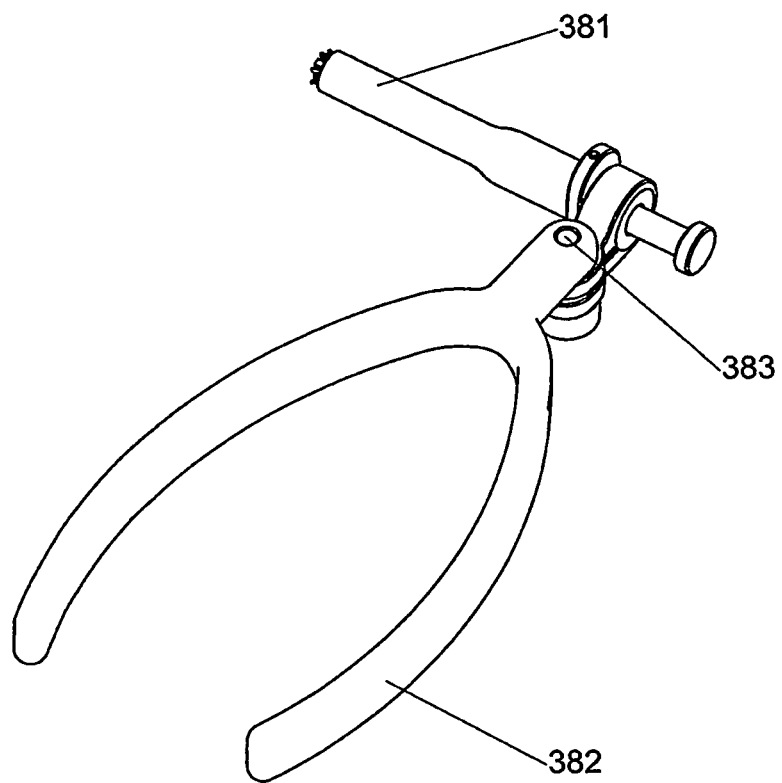
FIG. 27 shows a surgical fastening device in accordance with another embodiment of the invention attached to a handle at a hinge.

FIG. 27 shows that a fastening device 381 of the invention may be attached to a handle 382 at an adjustable hinge 383, permitting deploying a fastener at any desired angle. The fastening device 381 may be any fastening device in accordance with the invention.

Figure 28:
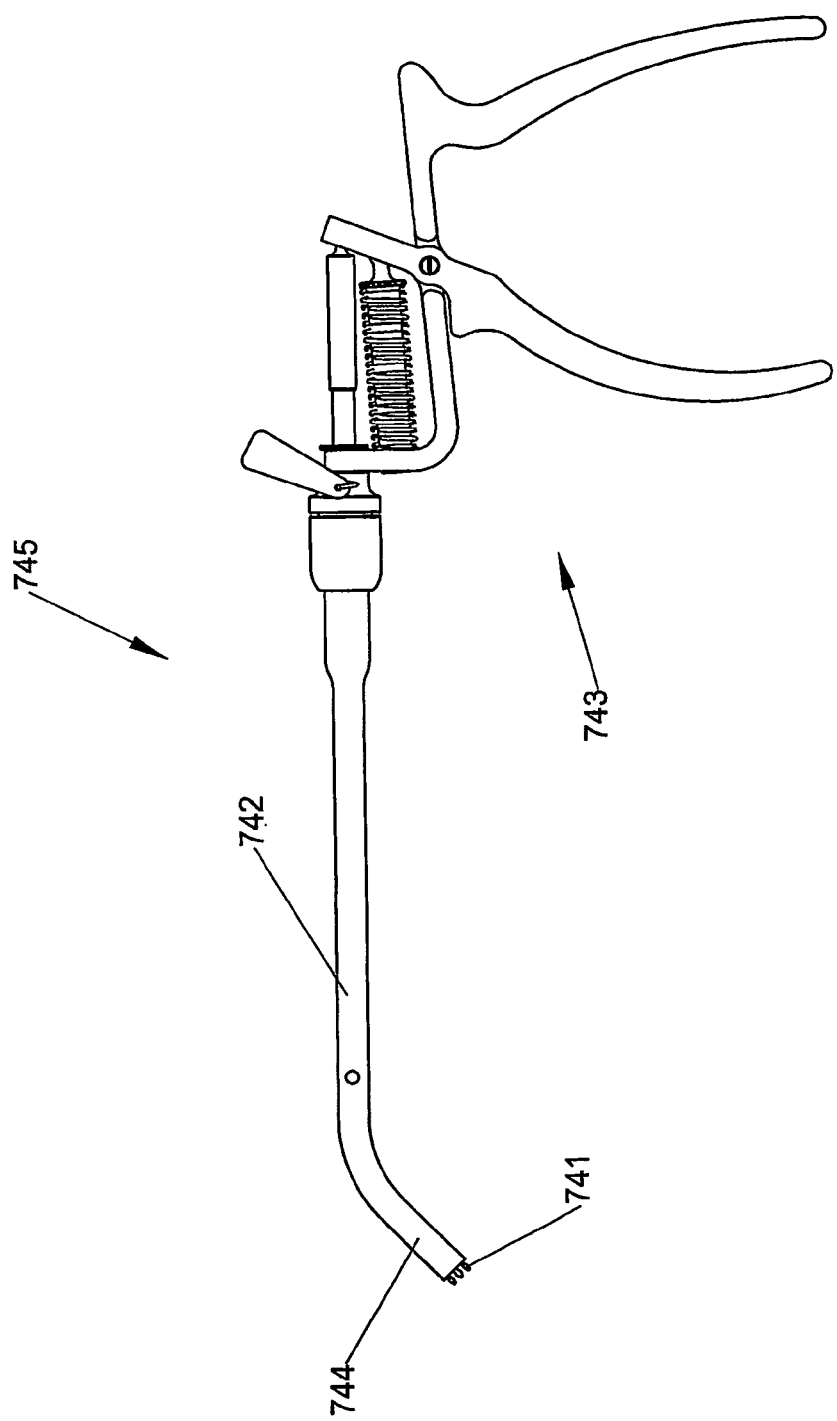
FIG. 28 shows a surgical fastening device having protrusions at its distal end for grasping a surgical mesh in accordance with another embodiment of the invention.

FIG. 28 shows another embodiment 745 of the surgical fastening device of the invention. The fastening device 745 has a bent shaft 742 that extends from a handle portion 743. The shaft 742 can be rotated in the handle portion 743 in order to direct the distal end 744 of the shaft in any desired direction. The shaft 742 is preferably detachable from the handle portion 743.

The sheath of the shaft 742 may be provided at its distal end with axial protrusions 741 that are used to grasp a mesh material in order to bring it to a desired position on a tissue surface when the mesh is to be attached by a fastener of the invention. The protrusions 741 may be triangular in shape, pear shaped, rod-like, or any elongated shape.

Figure 29:
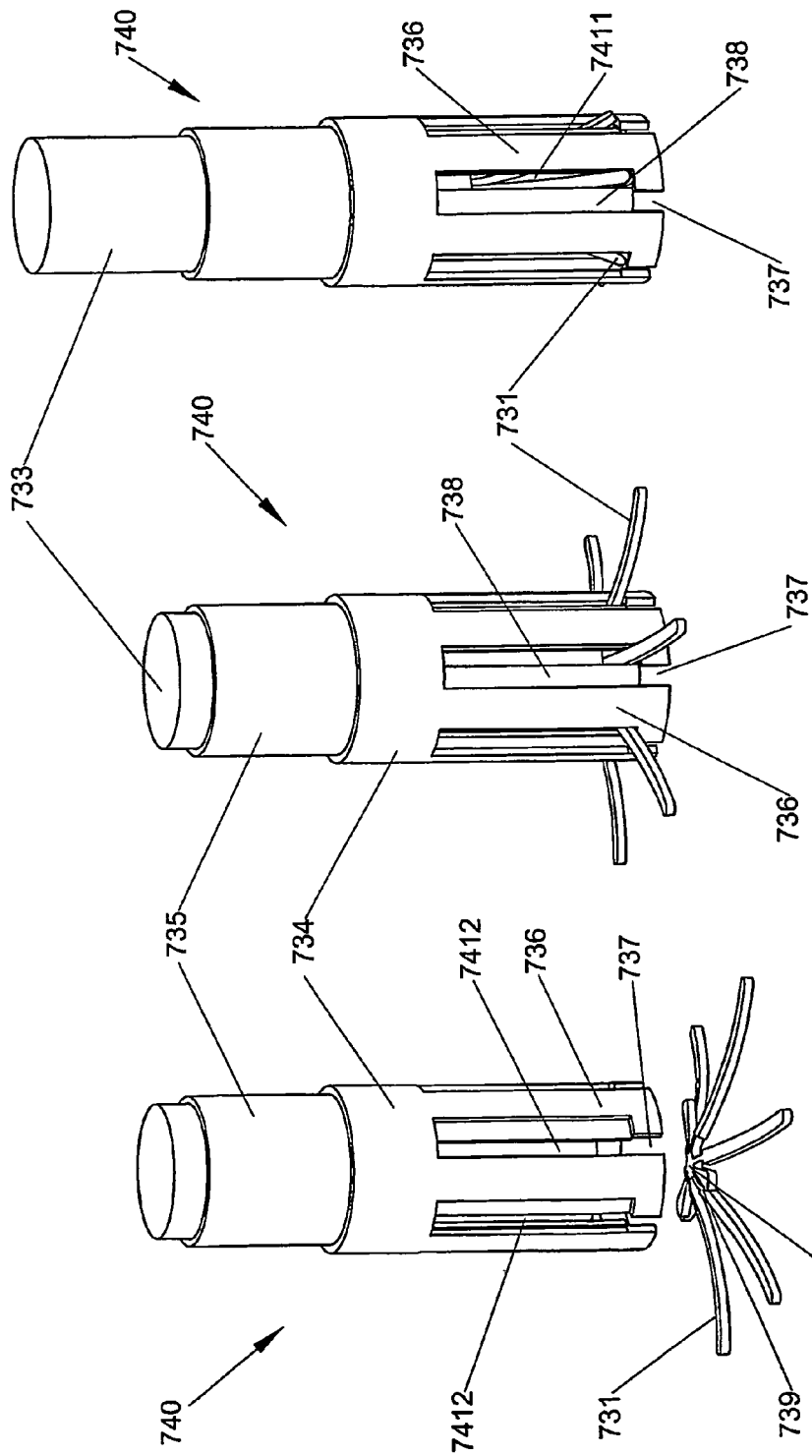
FIG. 29 shows the distal end of a surgical fastening device of the invention configured to deploy a surgical fastener not having a second element.

FIG. 29 shows an alternative structure for the distal end of a shaft 740 of the fastening device of the invention. This structure is used for deploying a surgical fastener 732 of the invention not having a baseplate, for example the fastener 70 shown in FIG. 8. A sheath 734 has "L" shaped projections 736 cut into its distal end separating slots 737. A sleeve 735 has straight projections 738 cut into its distal end separating straight slots 7412. In this structure, the sheath 734 and the sleeve 735 rotate in relation to one another. In one relative position of the sheath 734 and sleeve 735, blind slots 7411 are formed in the shaft 740 on the lateral side of the distal end of shaft as shown in FIG. 29a. Prongs 731 of the fastener 739 are forced through the blind slots 7411 when a plunger 733 is moved distally inside the sleeve 735 to push the crown 732 (not visible in FIGS. 29a and b) distally inside the sleeve 735. As the crown 732 moves distally in the sleeve 735, the prongs 731 splay out (FIG. 29b) as the fastener 739 attains its deployed configuration. In order to release the fastener 739 from the fastening device, the sheath 734 is rotated about the sleeve 735 to generate open slots 737 at the distal end of the shaft 740 through which the prongs can pass, as shown in FIG. 29c. The fastening device can then be removed from the body.

Figure 30:
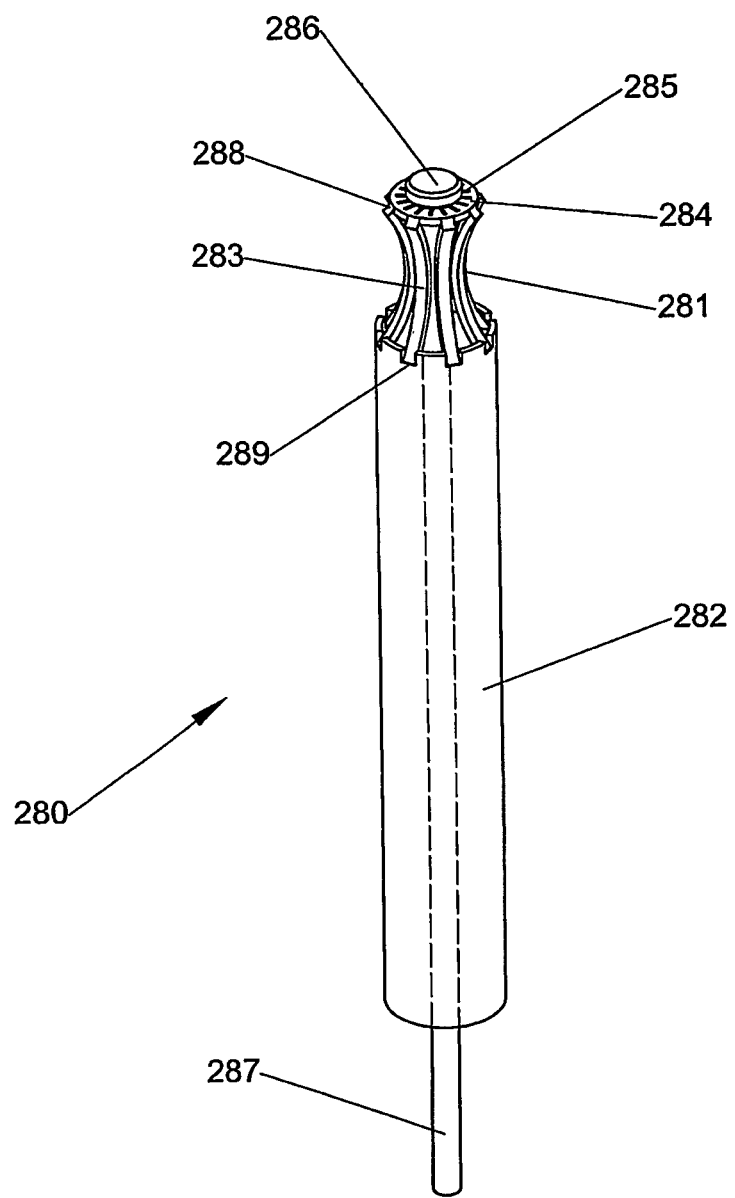
FIG. 30 shows the distal end of a surgical fastening device of the invention configured to deploy a surgical fastener not having a second element, in accordance with another embodiment of the invention.

FIG. 30 shows an alternative structure for the distal end of a shaft 280 of the fastening device of the invention. This structure is used for deploying a surgical fastener 281 of the invention not having a baseplate, for example the fastener 70 shown in FIG. 8. The fastener 281 is positioned at the distal end of a sleeve 282 with prongs 283 facing proximally. A crown 284 of the fastener 281 has a central hole 285 to which is attached a knob 286, on its distal aspect. The holding means is attached to an axial filament or rod 287 longitudinally traversing the sleeve to the proximal end and serves for pulling the fastener against the distal edge 287 of the sleeve 282. As the filament or rod 287 is pulled proximally, a force is applied to the prongs 283 by the edge 287 of the distal end of the sleeve 282 causing the prongs to rotate at hinge regions 288 and to splay radially outward and penetrate a covering or mesh and/or tissue, as the fastener 281 attains its deployed configuration. After deployment, the knob 286 and filament or rod 287 may be left within the body or the filament or rod 287 may be cut.

Figure 31:
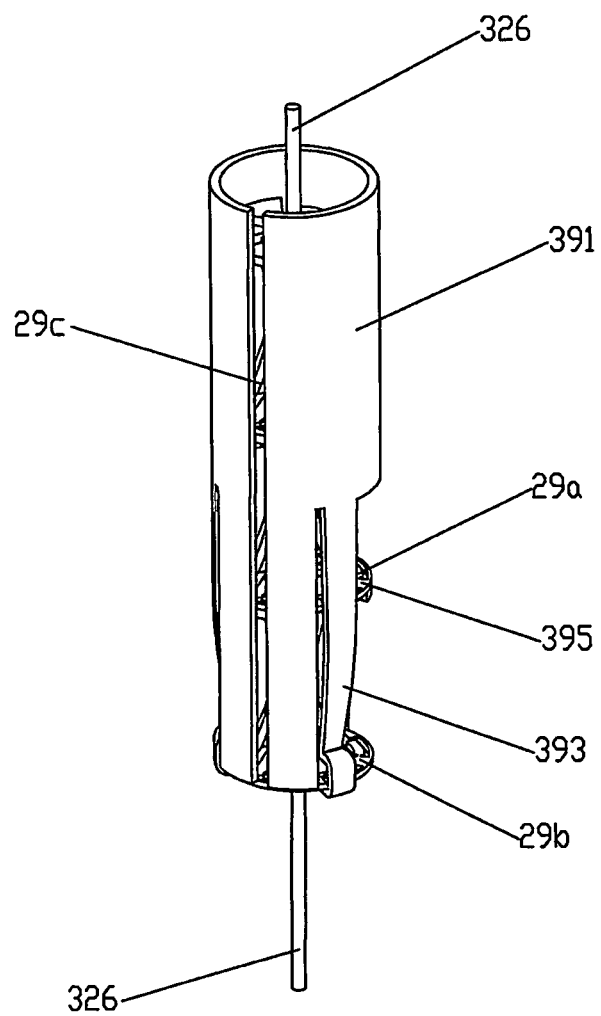
FIG. 31 shows the distal end of a surgical fastening device of the invention configured to deploy a surgical fastener together with a surgical filament.

FIG. 31 shows an alternative structure for the distal end of a shaft of the fastening device of the invention. A sleeve 391 inside the shaft is adapted to receive and deploy two or more surgical fasteners of the invention such as fasteners 29a, 29b, and 29c. The fasteners are stacked one above another inside the sleeve 391, and a plunger (not shown in FIG. 31) is used to push upon the proximal-most fastener in a distal direction. The force is transmitted through the stack of fasteners to the distal-most fastener 29b. The fastening device may be provided with a mechanism, such that when the penultimate fastener 29a presses the distal-most fastener 29b, the stack of fasteners moves distally and the baseplate 395 of the penultimate fastener 29a pushes S shaped stops 393 radially outward to release the deployed fastener.

Figure 32:
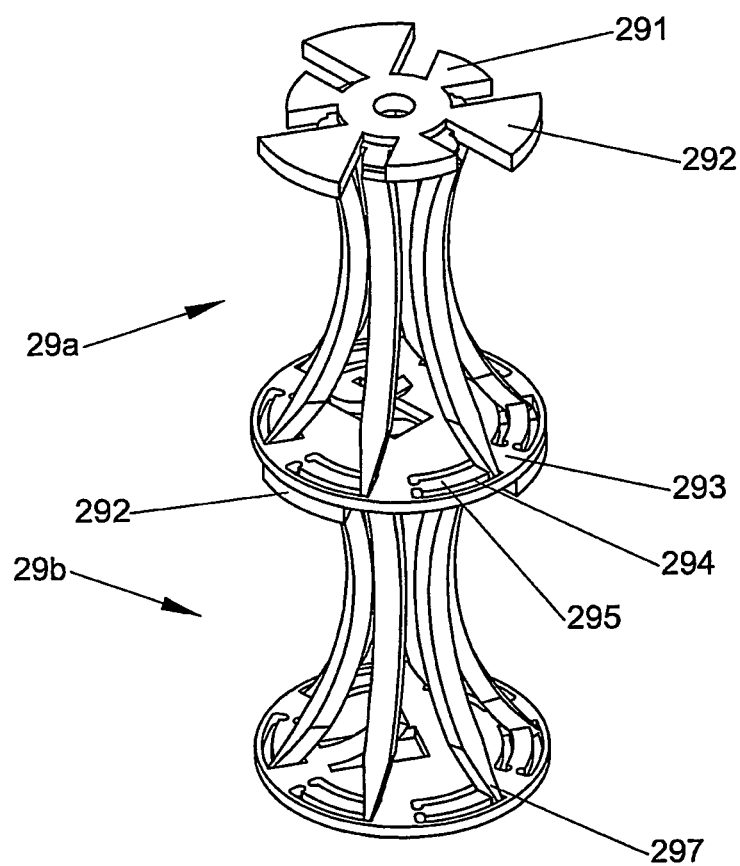
FIG. 32 shows a stack of surgical fasteners of the invention.

FIG. 32 shows the stack of fasteners alone. The fasteners 29a and 29b are provided with a mechanism to prevent premature outward extension of the prongs of all of the fasteners in the stack except for the distal-most fastener 29b during application of an axial force through the entire stack of fasteners by the plunger. Premature extension of the prongs may prevent passage of the stack of fasteners through the sleeve by jamming of the prongs into the sleeve wall. A baseplate 293 of each fastener has slots 294 provided with a leaflet 295 that is connected to the baseplate 293. A crown 291 of each fastener is provided with radial projections 292. A space between the leaflet 295 and the edge of the slot 294 permits only the tip of the prongs to pass while obstructing the passage of the shaft of the prongs through the slots 294 due to its larger width. When an axial force is applied to the distal most fastener 29b, a force is applied between the tips 297 of the prongs and the leaflets 295, causing the leaflets 295 to rotate and extend downward, opening the space between the leaflets and the edge of the slots 294, and permitting the prongs to pass through the slots. However, the other fasteners in the stack, such as the fastener 29a, are oriented so that the crown projections 292 of the fastener 29b are situated beneath the leaflets of the fastener 29a. Thus, when an axial compression force is applied through the fasteners other than the distal most fastener, the projections of the crown of the underlying fastener support the leaflets of the slots of the overlying fastener and prevent them form projecting downwardly and preventing the prongs from passing through the slots.

Another mechanism for preventing premature deployment of a fastener in a stack of fasteners is to fill the baseplate slots with a plug of a material such as a biodegradable plastic material. The slots with their plugs of a fastener are supported by the projection of the crown of the underlying fastener, except for the slots of the distal most fastener. When a force is applied to the distal-most fastener by the plunger, the prongs are forced through the slots pushing out the plugs.

Figure 33:
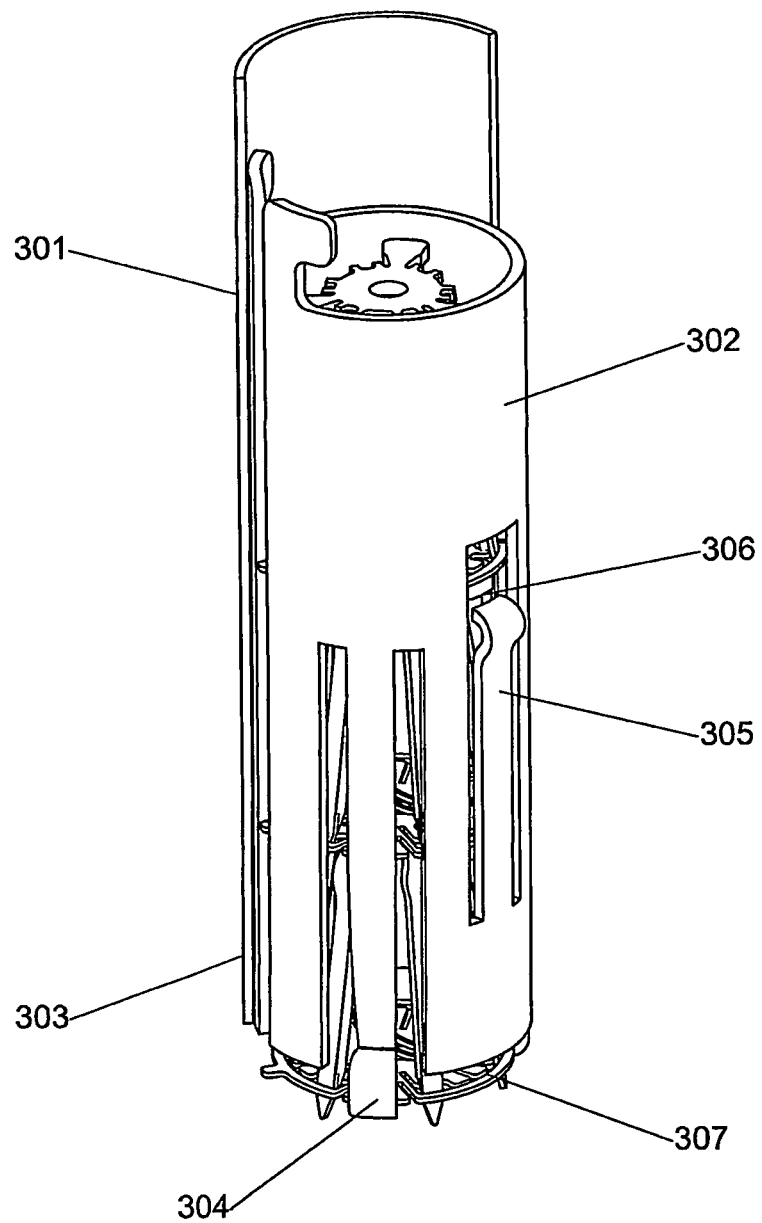
FIG. 33 shows the distal end of a surgical fastening device of the invention configured to deploy the surgical fasteners of FIG. 32.
Figure 34A:
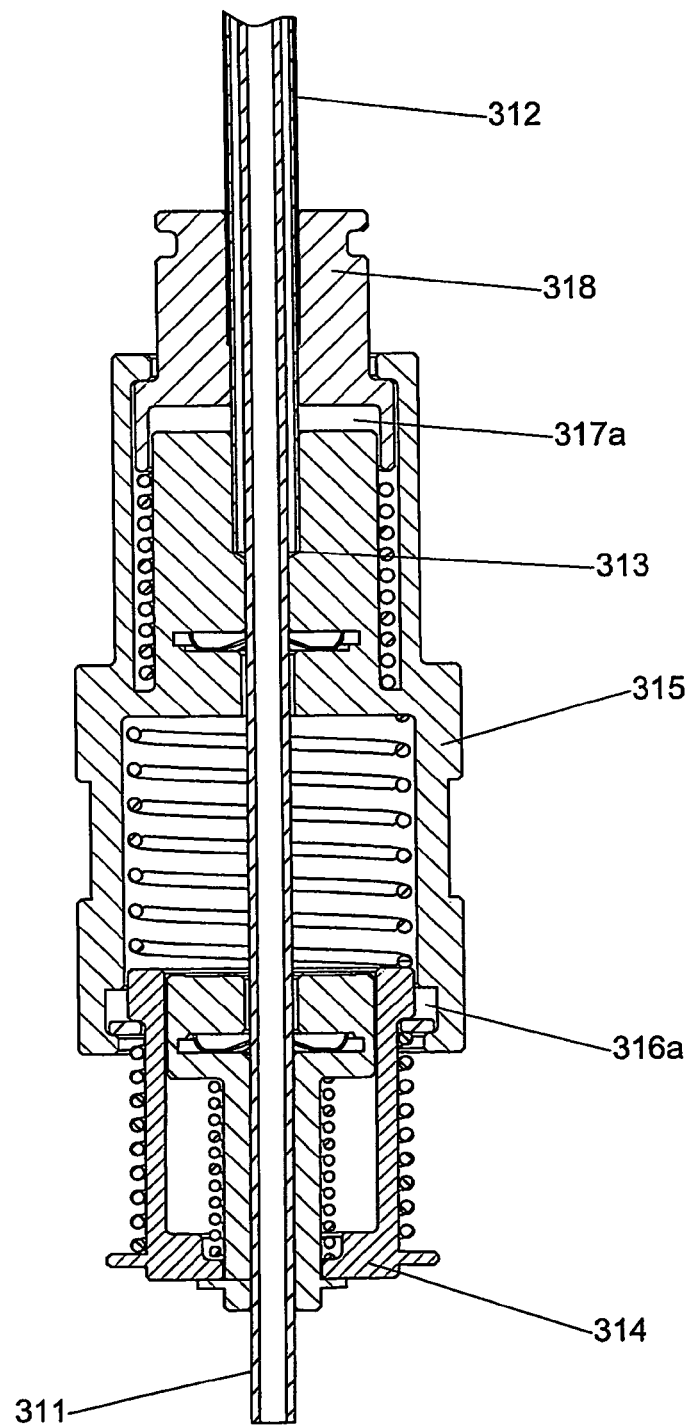
FIG. 34 shows the mechanism of a surgical fastening device during deployment of a surgical fastener according to yet another embodiment of the invention.
Figure 34B:
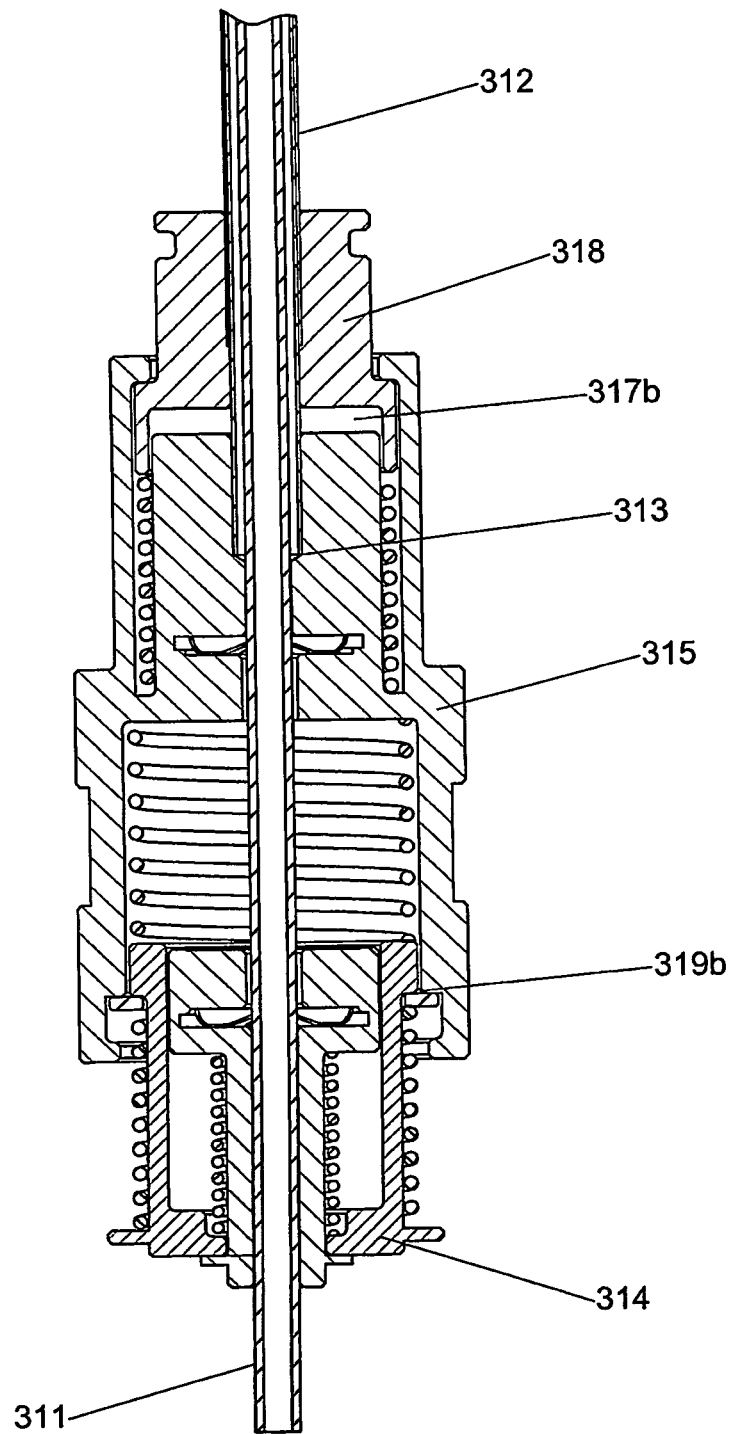
Figure 34C:
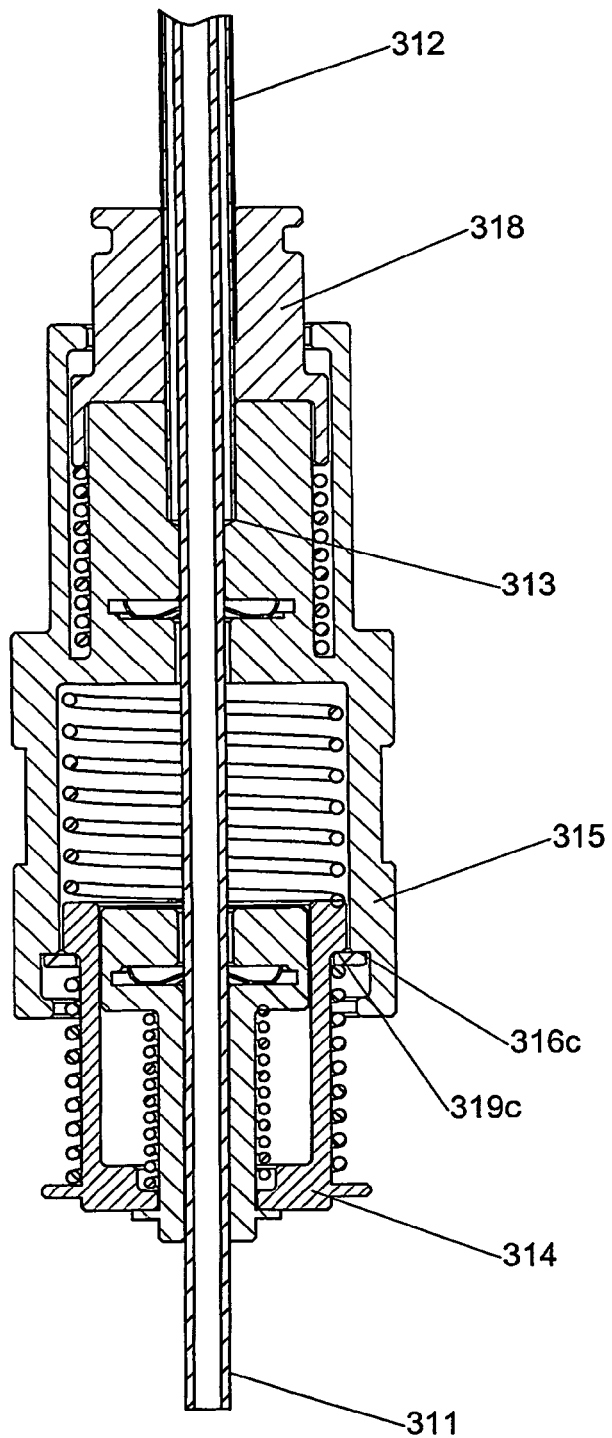
Figure 34D:
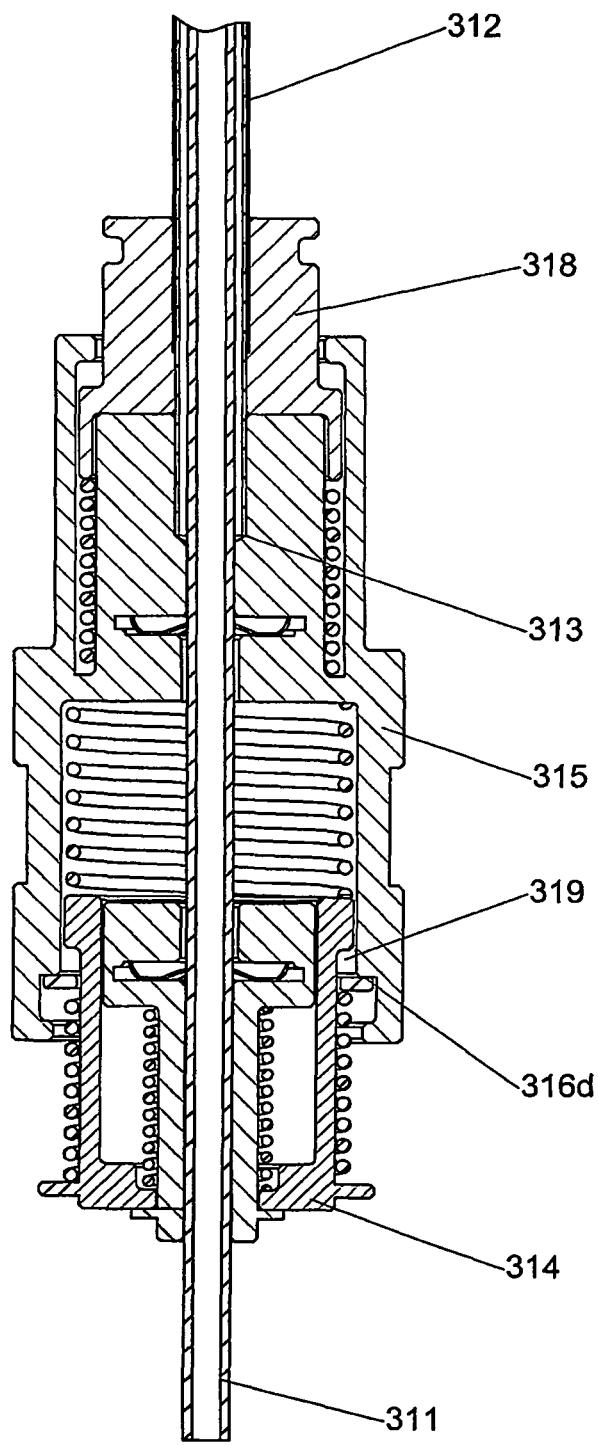
Figure 34E:
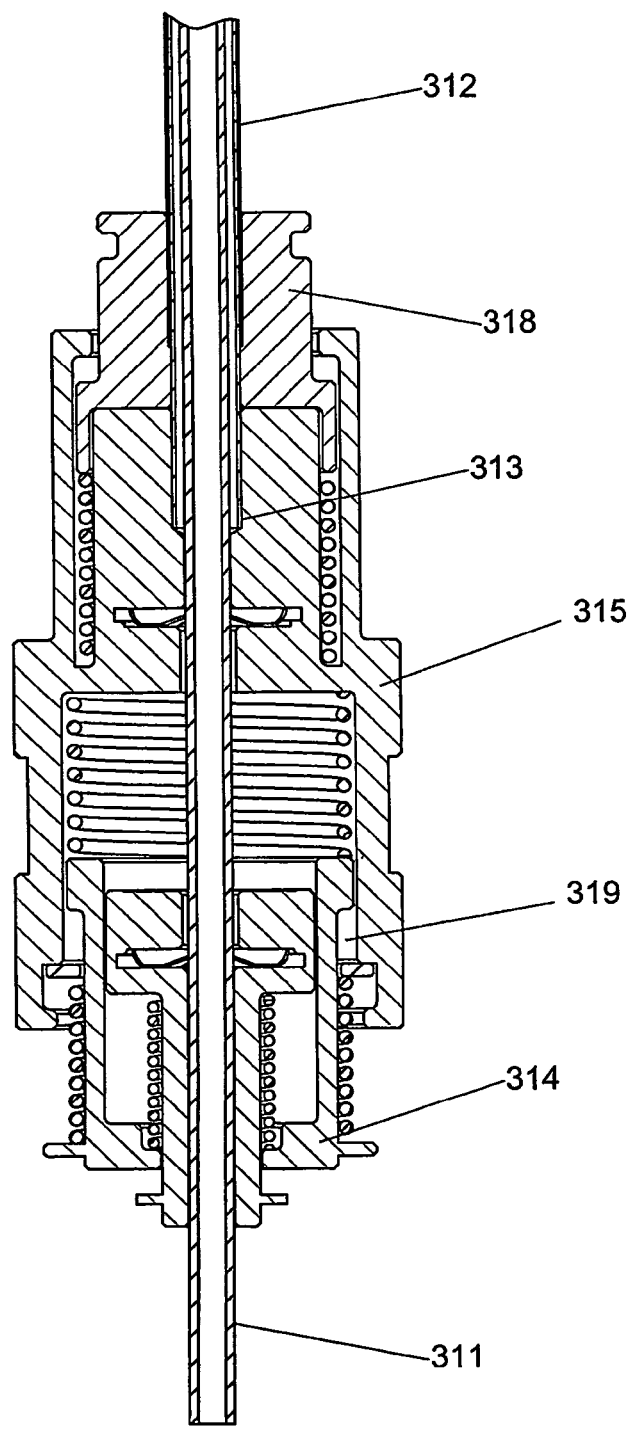

FIG. 33 shows yet another alternative structure for the distal end of the fastening device of the invention. In this structure, a sleeve 302 is provided. A distal segment 303 of an outer sheath 301 constrains stops 304 of the distal end of a sleeve 302 from moving radially outward. A plunger (not shown in FIG. 33) is provided with a ratchet mechanism that permits only distally directed movement of the stack of fasteners within the sleeve 302. One or more inner projections 305 are cut in the wall of the sleeve 302 at the distal end of the sleeve that prevent ejection of the remaining fasteners 306 during release of the distal-most fastener 307 in its deployed configuration. In this case, the distal-most fastener may be deployed and released using one continuous movement of a lever provided in the handle of the fastening device.

FIG. 34 shows a deployment mechanism for a fastening device of the invention. A handle has a housing in which a plunger 311, sleeve 313 and sheath 312 are coupled through springs of predetermined length and strength. By compressing a lever (not shown in FIG. 34), the plunger 311 is advanced distally compressing the distal-most fastener through the stack of fasteners. An encasement 314 attached to the plunger 311 is urged against the encasement 315 attached to the sleeve 313 closing a space 316a to bring the device to the configuration shown in FIG. 34b. The sleeve encasement 315 is thus engaged and is caused to move distally relative to the sheath encasement 318, closing a space 317a between them to bring the device to the configuration shown in FIG. 34c but without releasing stops (such as the stops 304 in FIG. 33) that hold the distal most fastener. This movement constrains an inner blocking protrusion (such as the protrusions 305 shown in FIG. 33) to move medially. Continuing to press the lever further advances the plunger 311 within the sleeve 313 and further compress the distal-most fastener against the stops as it acquires its deployed configuration with the prongs fully splayed while preventing the other fasteners from being deployed due to the blocking protrusion. This advancement of the plunger within the sleeve brings the device to the configuration shown in FIG. 34d by the advancement of the plunger encasement 314 in relation to the sleeve encasement 315 and opening a space 319. With continued depression of the lever, the force exerted by the plunger exerts a pressure on the distal-most fastener, while releasing the constraint on the distal stops so as to eject the distal-most fastener. This brings the device to the configuration illustrated in FIG. 34e in which the encasement of the plunger 314 has advanced inside the encasement of the sleeve 315, increasing the space 319.

Figure 35:
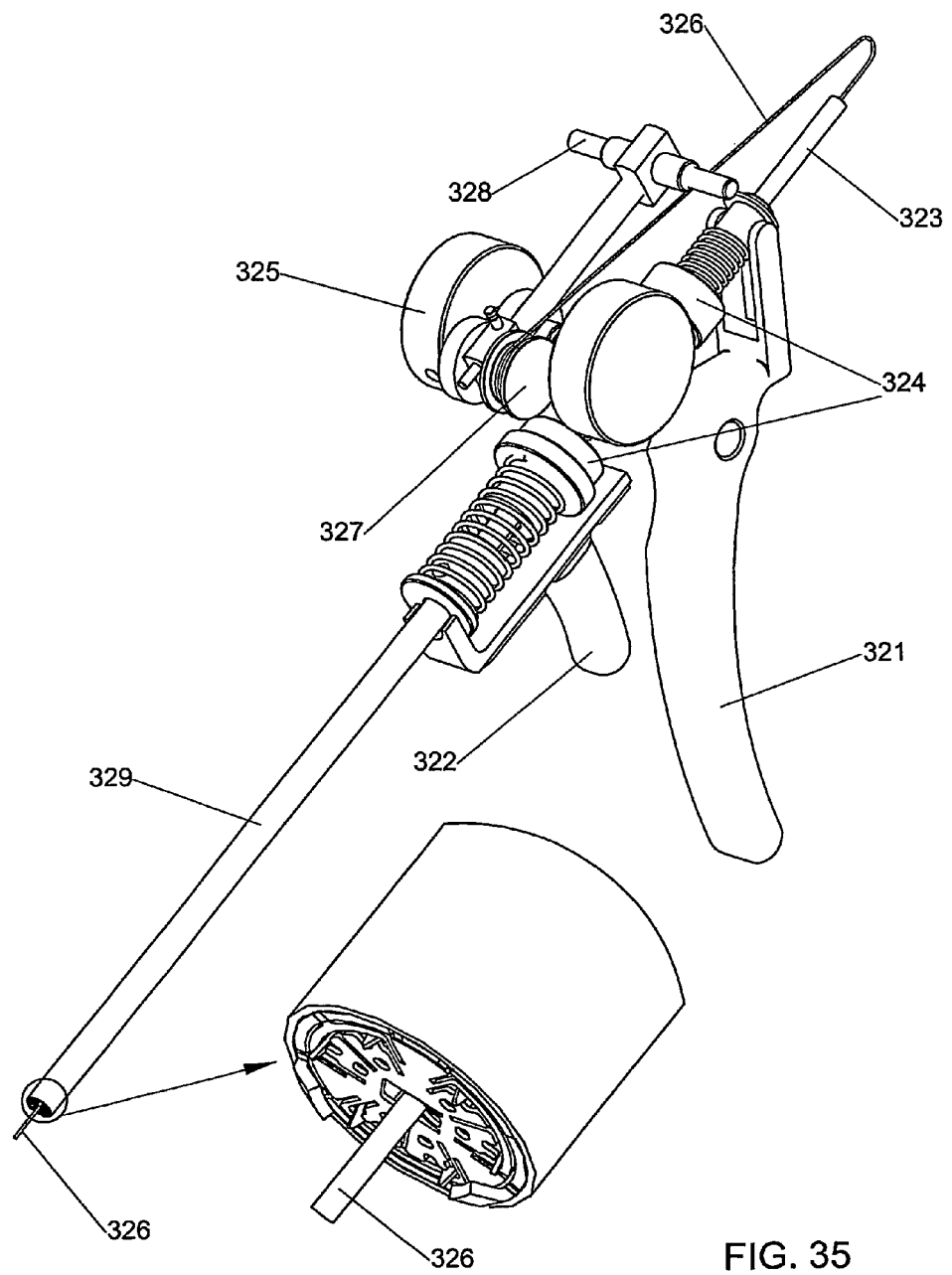
FIG. 35 shows a surgical fastening device having a surgical filament delivery system in accordance with another embodiment of the invention.

FIG. 35 shows another deployment mechanism for deploying a fastener of the invention. A first lever 321 is used to deploy the distal-most fastener in a stack of fasteners and a second lever 322 is used to release the fastener from the fastening device. The lever 321 acts on a plunger 323 through a ratchet mechanism 324 and applies a force to a distal-most fastener to achieve compression of the distal-most fastener against stops and to bring the distal-most fastener to its deployed configuration. The lever 322 is connected to the proximal end of an outer sheath 329 that can move proximally relative to the sleeve resulting in release of the deployed fastener.

A thread or filament 326 that passes through the stack of fasteners is grasped between the crown and baseplate of the deployed fastener. The thread 326 is wound on a drum 327 that may be locked or released by an actuating knob 328. When too much thread has been released, the drum 327 can be rotated by a knob 325, rewinding the excess thread. FIG. 31 shows the distal end of the shaft with a filament passing through the stack of fasteners.

Figure 36:
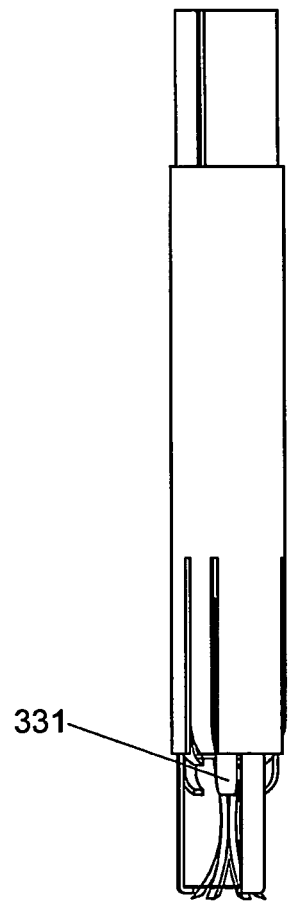
FIG. 36 shows the distal end of a surgical fastening device according to another embodiment of the invention.
Figure 37:
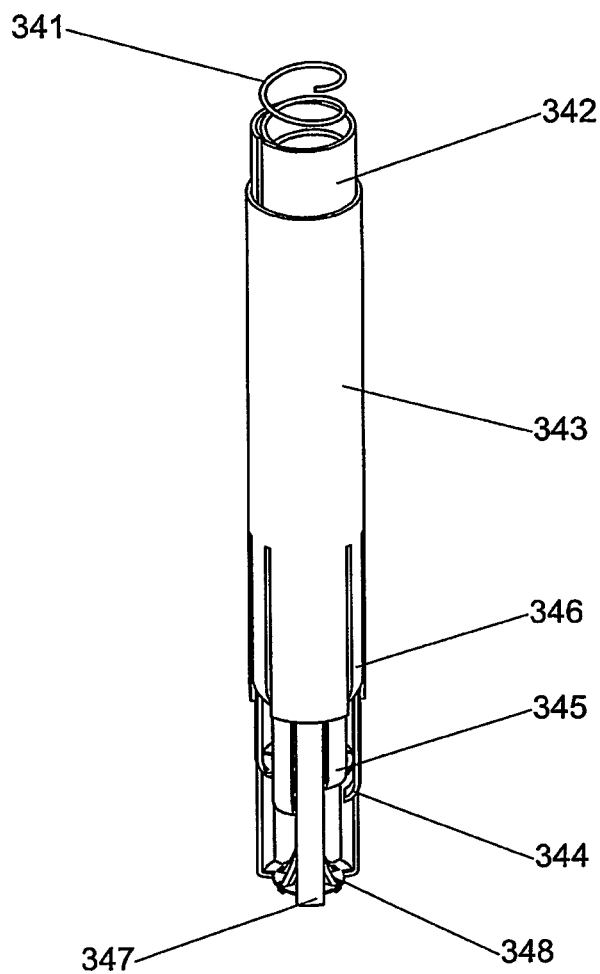
FIG. 37 shows the distal end of a surgical fastening device according to another embodiment of the invention in which surgical fasteners move towards the distal end under the influence of a spring.
Figure 38:
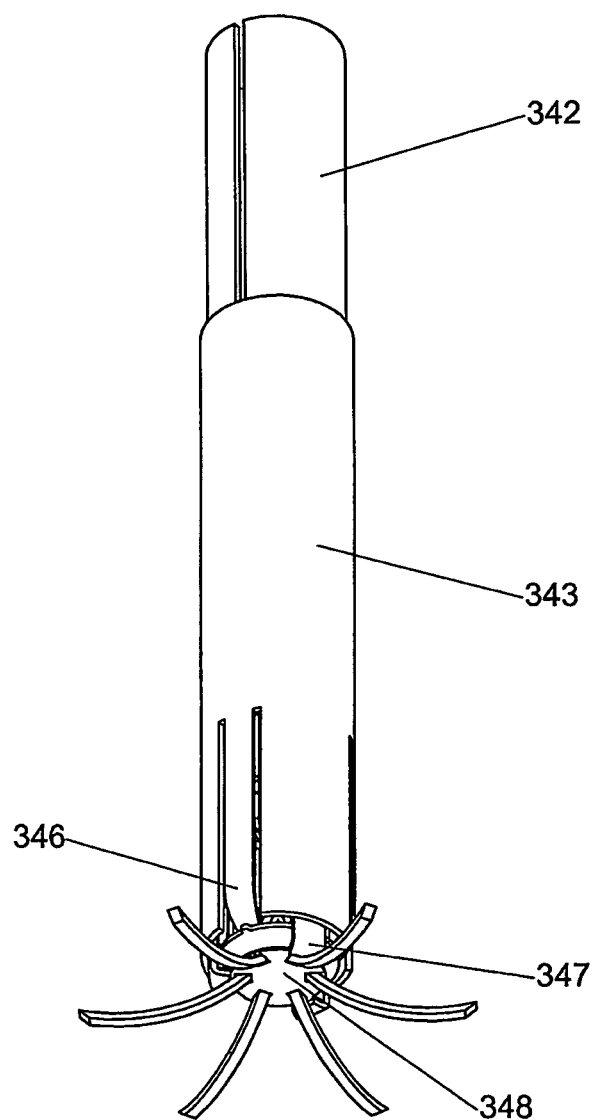
FIG. 38 shows deployment of a surgical fastener by the surgical fastening device of FIGS. 37 and 38.

FIGS. 36, 37, and 38 show another embodiment of the fastening device of the invention. A compressed spring 341, serves to advance a stack of fasteners distally. A sleeve 342 is provided with stops 344 at its distal end that prevent ejection of fasteners other than the distal-most fastener and stops 345 that prevent the distal-most fastener 348 from moving proximally inside the shaft. The distal-most fastener 348 is grasped by stops 346 of a sheath 343 and compressed against stops 347 of the sleeve. Retracting a sheath 343 removes the constraint on the stops 347 and permits the release of the deployed distal-most fastener 348.

Figure 39:
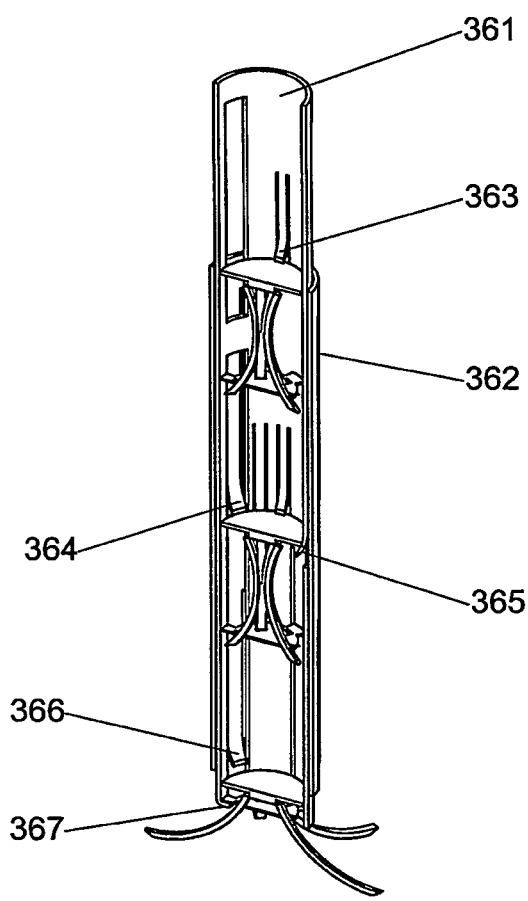
FIG. 39 shows the distal end of a surgical fastening device according to another embodiment of the invention having a ratchet mechanism for moving surgical fasteners in a distal direction while preventing movement of surgical filaments in a proximal direction.
Figure 40:
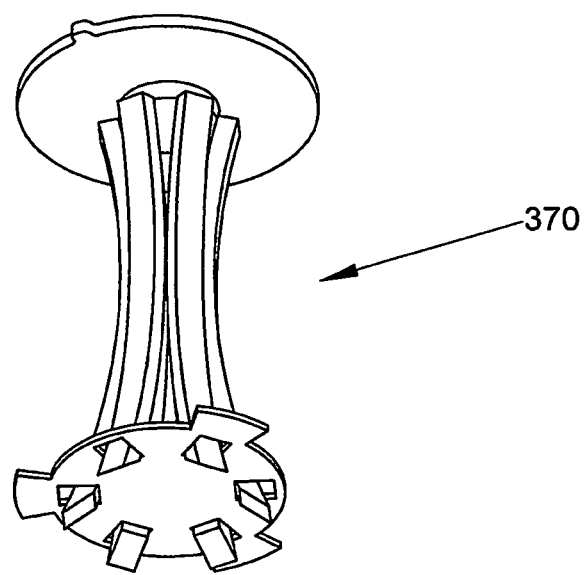
FIG. 40 shows a surgical fastener for use with the surgical fastening device of FIGS. 36, 37, 38, and 39.

FIG. 39 shows another possible structure of the shaft having a ratchet mechanism to promote movement of the fasteners in the shaft. Inner projections 363 and 365 from a sleeve 361 and inner projections 364, from an outer sheath 362 permit only distal movement of the fasteners shown in FIG. 40, with every reciprocating movement of the sheath 362 in the sleeve. The distal-most of these projections 366 from the sheath 362 serves as a plunger and thus serves to compress the distal-most fastener against stops 367.

The invention claimed is:

1. A surgical fastener having an undeployed configuration and a deployed configuration, the surgical fastener comprising:
   a first element having a peripheral edge radially spaced from a longitudinal axis of the surgical fastener;
   more than two prongs, each prong being attached to the first element in spaced relationship from each other along said peripheral edge at a respective hinge defined by a weakened region of each prong, and each prong having a tip; and
   a second element comprising a plate having preformed slots, the tips of the prongs being engaged in respective slots of the preformed slots when the surgical fastener is in the undeployed configuration prior to engagement with body tissue,
   wherein, in the undeployed configuration of the surgical fastener, the tip of each prong is located at a first distance from the longitudinal axis and each hinge is located at a second distance from the longitudinal axis, wherein the first distance is greater than the second distance,
   wherein, in the deployed configuration of the surgical fastener, the tip of each prong is located at a third distance from the longitudinal axis that is greater than the first distance,
   wherein the surgical fastener is locked in the deployed configuration by an engagement between the second element and the prongs, and
   wherein the surgical fastener is configured to move from the undeployed configuration to the deployed configuration.

2. The surgical fastener according to claim 1 configured to attain the deployed configuration by extending the prongs at the hinges when an extending force is applied to the prongs.

3. The surgical fastener according to claim 1 wherein the prongs have a profile selected from the group consisting of a rectangular profile, a round profile, an oval profile, a triangular profile and an elliptical profile.

4. The surgical fastener according to claim 1 wherein the prongs have a shape selected from the group consisting of a straight shape, a curved shape with constant curvature and a curved shape with variable curvature.

5. The surgical fastener according to claim 1 wherein the prong tips have a configuration selected from the group consisting of a blunt tip, a pointed tip and a barbed tip.

6. The surgical fastener according to claim 1 being configured to adopt the deployed configuration when the first element is urged along the longitudinal axis towards the second element.

7. The surgical fastener according to claim 1, wherein the first element has a shape selected from the group consisting of a flat disk, a polygonal shaped flat surface, an irregularly shaped flat surface, an annular ring, a cylindrical ring, and a cylinder.

8. The surgical fastener according to claim 1 wherein the second element has a shape selected from the group consisting of a flat disk, a polygonal shaped flat surface, an irregularly shaped flat surface, an annular ring, a cylindrical ring, and a cylinder.

9. The surgical fastener according to claim 1 wherein the first element is provided with a hole.

10. The surgical fastener according to claim 1 further comprising a surgical filament attached to the fastener.

11. The surgical fastener according to claim 1, wherein the second element comprises a flat plate.

12. The surgical fastener according to claim 1, wherein the first element comprises a plate.

13. The surgical fastener according to claim 1, wherein the first element comprises a flat plate.

14. The surgical fastener according to claim 1, wherein the weakened portion of each prong comprises a region of reduced thickness or width.

15. The surgical fastener according to claim 1 wherein the hinges between the first element and the prongs are integral hinges.

16. The surgical fastener according to claim 15 wherein the integral hinges between the first element and the prongs consist of the weakened region of the prongs.

17. The surgical fastener according to claim 15 wherein the integral hinges between the first element and the prongs consist of an adhesive.

18. The surgical fastener according to claim 1 wherein the second element is provided with a hole.

19. The surgical fastener according to claim 18 wherein the hole in the second element is provided with a flap configured to grasp a surgical filament passing through the hole in the second element when the fastener is in the deployed configuration.

20. The surgical fastener according to claim 1 wherein the first element is provided with a first hole and the second element is provided with a second hole.

21. The surgical fastener according to claim 20 wherein the first hole and the second hole are not coaxial.

* * * * *